United States Patent
Gavish

(10) Patent No.: US 10,576,355 B2
(45) Date of Patent: Mar. 3, 2020

(54) GENERALIZED METRONOME FOR MODIFICATION OF BIORHYTHMIC ACTIVITY

(75) Inventor: Benjamin Gavish, Mevasseret Zion (IL)

(73) Assignee: 2BREATHE TECHNOLOGIES LTD., Eshtaol (IL)

( * ) Notice: Subject to any disclaimer, the term of this patent is extended or adjusted under 35 U.S.C. 154(b) by 1788 days.

(21) Appl. No.: 10/524,056

(22) PCT Filed: Aug. 6, 2003

(86) PCT No.: PCT/IL03/00649
§ 371 (c)(1),
(2), (4) Date: Sep. 26, 2005

(87) PCT Pub. No.: WO2004/014226
PCT Pub. Date: Feb. 19, 2004

(65) Prior Publication Data
US 2006/0102171 A1    May 18, 2006

Related U.S. Application Data

(60) Provisional application No. 60/402,378, filed on Aug. 9, 2002.

(51) Int. Cl.
*A63B 71/06* (2006.01)
*A63B 23/18* (2006.01)
(Continued)

(52) U.S. Cl.
CPC ........ *A63B 71/0686* (2013.01); *A61B 5/0816* (2013.01); *A61B 5/486* (2013.01);
(Continued)

(58) Field of Classification Search
CPC ........... A61M 2021/005; A61B 5/4857; A63B 23/185
See application file for complete search history.

(56) References Cited

U.S. PATENT DOCUMENTS

| | | |
|---|---|---|
| 3,942,404 A | 3/1976 | Del Castillo |
| 3,945,292 A | 3/1976 | Del Castillo |
| (Continued) | | |

FOREIGN PATENT DOCUMENTS

| | | |
|---|---|---|
| EP | 0 856 334 | 8/1998 |
| GB | 1359005 | 7/1974 |
| (Continued) | | |

OTHER PUBLICATIONS

Abstract by B. Gavish, "Repeated Blood Pressure Measurements may Probe Directly an Arterial Property", American Journal of Hypertension, May-Jun. 2000, 13 (4), Part 2:190A.
(Continued)

*Primary Examiner* — Lynsey C Eiseman
*Assistant Examiner* — Amanda L. Steinberg
(74) *Attorney, Agent, or Firm* — The Roy Gross Law Firm, LLC; Roy Gross

(57) ABSTRACT

Apparatus (20) for use with a subject (30) is provided, including a memory, storing a set of computer instructions, the memory adapted to have stored therein an initial form of a multi-phase biorhythmic activity pattern and an indication of a desired form of the multi-phase biorhythmic activity pattern, wherein a ratio of durations of two phases in the desired form is different from a ratio of durations of the respective phases in the initial form, and wherein at least one phase of the multi-phase biorhythmic activity pattern corresponds to a respective phase of a multi-phase biorhythmic activity of the subject (30). The apparatus (20) further includes a stimulus unit (38), adapted to execute the stored (Continued)

instructions and to generate responsive thereto a time-varying stimulus that: (a) is substantially not responsive to ongoing measurement of the multi-phase biorhythmic activity during generation of the time-varying stimulus, and (b) has a multi-phase pattern that is characterized by a series of transitional forms intermediate the initial form and the desired form that guide the subject (30) to modify the biorhythmic activity.

63 Claims, 6 Drawing Sheets

(51) Int. Cl.
*A61B 5/00* (2006.01)
*A61M 21/00* (2006.01)
*A61B 5/08* (2006.01)
*A63B 69/00* (2006.01)
*A61F 5/56* (2006.01)

(52) U.S. Cl.
CPC .......... *A61B 5/4818* (2013.01); *A61B 5/4857* (2013.01); *A61M 21/00* (2013.01); *A63B 23/185* (2013.01); *A61F 5/56* (2013.01); *A61M 2021/005* (2013.01); *A61M 2021/0027* (2013.01); *A63B 69/0028* (2013.01); *A63B 2208/12* (2013.01)

(56) References Cited

U.S. PATENT DOCUMENTS

| | | | |
|---|---|---|---|
| 3,991,304 A * | 11/1976 | Hillsman | A61B 5/087 128/905 |
| 3,991,648 A | 11/1976 | Karpowicz | |
| 3,996,833 A | 12/1976 | Del Castillo | |
| 4,012,901 A | 3/1977 | Jones, III | |
| 4,014,167 A | 3/1977 | Hasegawa et al. | |
| 4,018,131 A | 4/1977 | Cannon | |
| 4,033,332 A | 7/1977 | Hardway, Jr. et al. | |
| 4,070,944 A | 1/1978 | Del Castillo | |
| 4,090,355 A | 5/1978 | Morohoshi | |
| 4,102,332 A | 7/1978 | Gessman | |
| D249,936 S | 10/1978 | Ishida | |
| D253,399 S | 11/1979 | Harle | |
| 4,193,257 A | 3/1980 | Watkins | |
| 4,195,626 A | 4/1980 | Schweizer | |
| 4,204,400 A | 5/1980 | Morohoshi et al. | |
| 4,218,874 A | 8/1980 | Ishida et al. | |
| 4,237,549 A | 12/1980 | Harle | |
| 4,312,358 A | 1/1982 | Barney | |
| 4,333,172 A | 6/1982 | Chen | |
| 4,354,412 A | 10/1982 | Deutsch | |
| 4,380,185 A | 4/1983 | Holcomb | |
| 4,381,788 A | 5/1983 | Douglas | |
| 4,442,752 A | 4/1984 | Tsuchiya | |
| 4,450,843 A | 5/1984 | Barney et al. | |
| 4,462,297 A | 7/1984 | Dill et al. | |
| 4,474,185 A | 10/1984 | Diamond | |
| 4,526,078 A | 7/1985 | Chadabe | |
| 4,571,680 A | 2/1986 | Wu | |
| 4,580,574 A | 4/1986 | Gavish | |
| 4,583,443 A | 4/1986 | Senghaas et al. | |
| 4,602,551 A | 7/1986 | Firmani et al. | |
| 4,612,841 A | 9/1986 | Yoshikawa | |
| 4,629,331 A | 12/1986 | Harle | |
| 4,649,794 A | 3/1987 | George | |
| 4,672,849 A | 6/1987 | Hoshino | |
| 4,711,585 A | 12/1987 | Fresquez et al. | |
| 4,733,593 A | 3/1988 | Rothbart | |
| D295,728 S | 5/1988 | Berry | |
| 4,759,253 A | 7/1988 | Harle et al. | |
| 4,776,323 A | 10/1988 | Spector | |
| 4,798,538 A | 1/1989 | Yagi | |
| 4,819,656 A * | 4/1989 | Spector | A61B 5/486 128/905 |
| 4,827,943 A | 5/1989 | Bornn et al. | |
| 4,883,067 A | 11/1989 | Knispel et al. | |
| 4,974,483 A | 12/1990 | Luzzatto | |
| 4,981,295 A * | 1/1991 | Belman | A61B 5/087 482/13 |
| 4,982,642 A | 1/1991 | Nishikawa et al. | |
| D315,518 S | 3/1991 | Saito | |
| 5,027,686 A | 7/1991 | Ishikawa | |
| D319,791 S | 9/1991 | Saito | |
| 5,052,400 A | 10/1991 | Dietz | |
| 5,070,321 A | 12/1991 | Einhorn et al. | |
| 5,076,281 A | 12/1991 | Gavish | |
| D323,469 S | 1/1992 | Saito | |
| 5,131,399 A | 7/1992 | Sciarra | |
| 5,137,501 A | 8/1992 | Mertesdorf | |
| 5,143,078 A | 9/1992 | Mather et al. | |
| 5,167,610 A * | 12/1992 | Kitado et al. | 600/26 |
| 5,195,528 A | 3/1993 | Hok | |
| 5,214,228 A | 5/1993 | Hoiles et al. | |
| 5,234,392 A * | 8/1993 | Clark | A63B 69/0035 482/112 |
| 5,267,942 A | 12/1993 | Saperston | |
| D343,186 S | 1/1994 | Omuro | |
| 5,280,651 A | 1/1994 | Lenihan et al. | |
| 5,329,931 A | 7/1994 | Clauson et al. | |
| 5,343,871 A * | 9/1994 | Bittman et al. | 600/545 |
| D351,800 S | 10/1994 | Liao | |
| 5,367,292 A | 11/1994 | Szoke et al. | |
| 5,402,188 A | 3/1995 | Wayne | |
| 5,417,137 A | 5/1995 | Krasny et al. | |
| 5,423,328 A | 6/1995 | Gavish | |
| D360,143 S | 7/1995 | Omuro | |
| D360,144 S | 7/1995 | Omuro | |
| 5,434,871 A | 7/1995 | Purdham et al. | |
| 5,447,089 A | 9/1995 | Marrash | |
| 5,465,729 A | 11/1995 | Bittman et al. | |
| 5,485,850 A | 1/1996 | Dietz | |
| D368,949 S | 4/1996 | Evans et al. | |
| 5,509,414 A | 4/1996 | Hok | |
| 5,515,764 A | 5/1996 | Rosen | |
| 5,533,947 A | 7/1996 | Tomlinson et al. | |
| 5,564,429 A | 10/1996 | Bornn et al. | |
| 5,577,510 A | 11/1996 | Chittum et al. | |
| 5,586,088 A | 12/1996 | Vochezer | |
| 5,590,282 A | 12/1996 | Clynes | |
| 5,592,143 A | 1/1997 | Romney et al. | |
| 5,596,994 A | 1/1997 | Bro | |
| D378,899 S | 4/1997 | Ridinger | |
| 5,621,390 A | 4/1997 | Neal | |
| 5,662,117 A | 9/1997 | Bittman | |
| 5,671,733 A | 9/1997 | Raviv et al. | |
| 5,678,571 A | 10/1997 | Brown | |
| 5,687,291 A | 11/1997 | Smyth | |
| 5,690,691 A | 11/1997 | Chen et al. | |
| D388,340 S | 12/1997 | Ridinger | |
| 5,730,145 A | 3/1998 | Defares et al. | |
| 5,734,090 A | 3/1998 | Koppel et al. | |
| 5,751,825 A | 5/1998 | Myers et al. | |
| 5,752,509 A | 5/1998 | Lachmann et al. | |
| 5,755,674 A | 5/1998 | Watson | |
| D389,080 S | 6/1998 | Ridinger | |
| 5,782,878 A | 7/1998 | Morgan | |
| 5,794,615 A | 8/1998 | Estes | |
| 5,797,852 A | 8/1998 | Karakasoglu et al. | |
| 5,800,337 A | 9/1998 | Gavish | |
| 5,827,179 A | 10/1998 | Lichter et al. | |
| 5,830,107 A | 11/1998 | Brigliadoro | |
| 5,850,048 A | 12/1998 | Ruf | |
| 5,899,203 A | 5/1999 | Defares et al. | |
| 5,904,639 A * | 5/1999 | Smyser | A61B 5/225 482/1 |
| 5,921,890 A | 7/1999 | Miley | |
| 5,997,482 A * | 12/1999 | Vaschillo | A63B 71/0686 600/484 |
| 6,001,048 A | 12/1999 | Taylor | |
| 6,001,065 A | 12/1999 | De Vito | |
| 6,013,007 A | 1/2000 | Root et al. | |

(56) References Cited

U.S. PATENT DOCUMENTS

| | | |
|---|---|---|
| 6,015,948 A | 1/2000 | Yang |
| 6,047,203 A | 4/2000 | Sackner et al. |
| 6,050,940 A | 4/2000 | Braun et al. |
| 6,086,379 A | 7/2000 | Pendergast et al. |
| 6,090,037 A | 7/2000 | Gavish |
| 6,092,058 A | 7/2000 | Smyth |
| D430,045 S | 8/2000 | Omuro et al. |
| 6,106,481 A | 8/2000 | Cohen |
| D430,810 S | 9/2000 | Omuro et al. |
| 6,150,941 A | 11/2000 | Geiger et al. |
| 6,162,183 A * | 12/2000 | Hoover .................. 600/534 |
| 6,179,723 B1 | 1/2001 | Evans |
| 6,201,769 B1 | 3/2001 | Lewis |
| 6,212,135 B1 | 4/2001 | Schreiber |
| 6,230,047 B1 | 5/2001 | McHugh |
| 6,241,683 B1 | 6/2001 | Macklem et al. |
| 6,251,048 B1 | 6/2001 | Kaufman |
| 6,261,238 B1 | 7/2001 | Gavriely |
| 6,264,582 B1 * | 7/2001 | Remes ............... A63B 23/20 482/8 |
| D449,236 S | 10/2001 | Hopkins |
| 6,314,339 B1 * | 11/2001 | Rastegar ........... A63B 24/0003 600/561 |
| 6,345,202 B2 | 2/2002 | Richmond et al. |
| 6,407,324 B1 | 6/2002 | Hulcher |
| 6,416,471 B1 * | 7/2002 | Kumar et al. ............. 600/300 |
| 6,478,736 B1 | 11/2002 | Mault |
| 6,508,772 B2 * | 1/2003 | Vilozni ..................... 600/538 |
| 6,519,567 B1 | 2/2003 | Fujii |
| 6,561,908 B1 | 5/2003 | Hoki |
| 6,582,342 B2 | 6/2003 | Kaufman |
| 6,607,484 B2 | 8/2003 | Suzuki et al. |
| 6,620,106 B2 * | 9/2003 | Mault ..................... 600/532 |
| 6,626,843 B2 * | 9/2003 | Hillsman ................. 600/529 |
| 6,662,032 B1 | 12/2003 | Gavish et al. |
| 6,672,991 B2 | 1/2004 | O'Malley |
| 6,675,043 B1 | 1/2004 | Prutchi et al. |
| 6,726,636 B2 | 4/2004 | Der Ghazarian et al. |
| 6,740,046 B2 * | 5/2004 | Knapp et al. ............. 600/538 |
| 6,746,247 B2 | 6/2004 | Barton |
| 6,790,178 B1 * | 9/2004 | Mault et al. ............. 600/300 |
| 6,808,473 B2 | 10/2004 | Hisano et al. |
| 6,902,513 B1 | 6/2005 | McClure |
| 7,117,032 B2 * | 10/2006 | Childre ............ A61B 5/02405 600/545 |
| 7,455,622 B2 | 11/2008 | Watterson |
| 7,521,623 B2 | 4/2009 | Bowen |
| 7,544,880 B2 | 6/2009 | Takai |
| 7,616,097 B1 | 11/2009 | Whang |
| 7,683,252 B2 | 3/2010 | Oliver |
| 7,705,230 B2 | 4/2010 | Bowen |
| 7,728,215 B2 | 6/2010 | Miyajima |
| 7,737,353 B2 | 6/2010 | Sasaki |
| 7,738,935 B1 | 6/2010 | Turcott |
| 7,745,716 B1 | 6/2010 | Murphy |
| 7,766,794 B2 | 8/2010 | Oliver |
| 7,771,320 B2 | 8/2010 | Riley et al. |
| 7,789,800 B1 | 9/2010 | Watterson |
| 7,805,150 B2 | 9/2010 | Graham |
| 7,841,967 B1 | 11/2010 | Kahn |
| 7,867,142 B2 | 1/2011 | Kim |
| 7,872,188 B2 | 1/2011 | Willis |
| 7,927,253 B2 | 4/2011 | Vincent |
| 7,942,824 B1 | 5/2011 | Kayyali |
| 7,973,231 B2 | 7/2011 | Bowen |
| 7,985,164 B2 | 7/2011 | Ashby |
| 8,017,853 B1 | 9/2011 | Rice |
| 8,029,415 B2 | 10/2011 | Ashby |
| 8,033,959 B2 | 10/2011 | DiBenedetto |
| 8,038,576 B2 | 10/2011 | Farinelli |
| 8,082,920 B2 | 12/2011 | Hughes |
| 8,101,843 B2 | 1/2012 | Turner |
| 8,105,208 B2 | 1/2012 | Oleson |
| 8,162,804 B2 | 4/2012 | Tagliabue |
| 8,183,453 B2 | 5/2012 | Wagner |
| 8,200,323 B2 | 6/2012 | DiBenedetto |
| 8,221,290 B2 | 7/2012 | Vincent |
| 8,241,184 B2 | 8/2012 | Oleson |
| 8,251,874 B2 | 8/2012 | Ashby |
| 8,298,123 B2 | 10/2012 | Hickman |
| 8,311,654 B2 | 11/2012 | Sako |
| 2001/0054270 A1 | 12/2001 | Rice |
| 2002/0040601 A1 | 4/2002 | Fyfe |
| 2002/0042328 A1 | 4/2002 | Yoo |
| 2003/0059750 A1 | 3/2003 | Bindler et al. |
| 2003/0065272 A1 * | 4/2003 | Hillsman ................. 600/529 |
| 2003/0171189 A1 | 9/2003 | Kaufman |
| 2004/0015093 A1 * | 1/2004 | Knapp et al. ............. 600/538 |
| 2004/0077934 A1 | 4/2004 | Massad |
| 2004/0116784 A1 | 6/2004 | Gavish |
| 2004/0127335 A1 | 7/2004 | Watterson et al. |
| 2005/0113703 A1 | 5/2005 | Farringdon et al. |
| 2005/0126370 A1 | 6/2005 | Takai |
| 2005/0215397 A1 | 9/2005 | Watterson et al. |
| 2006/0084551 A1 | 4/2006 | Volpe, Jr. |
| 2006/0107822 A1 | 5/2006 | Bowen |
| 2006/0111621 A1 | 5/2006 | Coppi |
| 2006/0169125 A1 | 8/2006 | Ashkenazi |
| 2006/0243120 A1 | 11/2006 | Takai |
| 2006/0102171 A1 | 12/2006 | Gavish |
| 2006/0277474 A1 | 12/2006 | Robarts et al. |
| 2007/0033295 A1 | 2/2007 | Marriott |
| 2007/0044641 A1 | 3/2007 | McKinney |
| 2007/0060446 A1 | 3/2007 | Asukai |
| 2007/0074618 A1 | 4/2007 | Vergo |
| 2007/0113725 A1 | 5/2007 | Oliver |
| 2007/0113726 A1 | 5/2007 | Oliver |
| 2007/0118043 A1 | 5/2007 | Oliver et al. |
| 2007/0135264 A1 | 6/2007 | Rosenberg |
| 2007/0169614 A1 | 7/2007 | Sasaki |
| 2007/0203665 A1 | 8/2007 | Darley |
| 2007/0029059 A1 | 9/2007 | Schwartz et al. |
| 2007/0208531 A1 | 9/2007 | Darley |
| 2007/0219070 A1 | 9/2007 | Schwartz et al. |
| 2007/0270667 A1 | 11/2007 | Coppi et al. |
| 2008/0076637 A1 | 3/2008 | Gilley et al. |
| 2008/0077619 A1 | 3/2008 | Gilley et al. |
| 2008/0077620 A1 | 3/2008 | Gilley et al. |
| 2008/0090703 A1 | 4/2008 | Rosenberg |
| 2008/0096726 A1 | 4/2008 | Riley et al. |
| 2008/0171943 A1 | 7/2008 | Farringdon et al. |
| 2008/0183090 A1 | 7/2008 | Farringdon et al. |
| 2008/0188354 A1 | 8/2008 | Pauws et al. |
| 2008/0214358 A1 | 9/2008 | Ogg et al. |
| 2008/0254946 A1 | 10/2008 | Pauws et al. |
| 2008/0300109 A1 | 12/2008 | Karkanias et al. |
| 2008/0306619 A1 | 12/2008 | Cerra et al. |
| 2009/0024233 A1 | 1/2009 | Shirai et al. |
| 2009/0054741 A1 | 2/2009 | McAleer |
| 2009/0088876 A1 | 4/2009 | Conley et al. |
| 2009/0139389 A1 | 6/2009 | Bowen |
| 2009/0260506 A1 | 10/2009 | Saperston |
| 2009/0270744 A1 | 10/2009 | Prstojevich et al. |
| 2010/0037753 A1 | 2/2010 | Wagner |
| 2010/0186578 A1 | 7/2010 | Bowen |
| 2010/0217099 A1 | 8/2010 | LeBoeuf et al. |
| 2010/0279825 A1 | 11/2010 | Riley et al. |
| 2010/0286532 A1 | 11/2010 | Farringdon et al. |
| 2011/0003665 A1 | 1/2011 | Burton et al. |
| 2011/0016120 A1 | 1/2011 | Haughay et al. |
| 2011/0054290 A1 | 3/2011 | Derchak |
| 2012/0094806 A1 | 4/2012 | Danford |
| 2012/0225412 A1 | 9/2012 | Wagner |

FOREIGN PATENT DOCUMENTS

| | | |
|---|---|---|
| GB | 2035088 | 6/1980 |
| WO | 97/26822 | 7/1997 |
| WO | WO 97/26822 | 7/1997 |
| WO | WO 98/14116 | 4/1998 |
| WO | 9964095 A2 | 12/1999 |
| WO | WO 00/59580 | 10/2000 |
| WO | 01/02049 | 1/2001 |
| WO | WO 01/02049 | 1/2001 |

(56) References Cited

FOREIGN PATENT DOCUMENTS

| WO | 0119243 A1 | 3/2001 |
| WO | 0213697 A1 | 2/2002 |
| WO | 2004014226 A1 | 2/2004 |

OTHER PUBLICATIONS

D.R. Begault, "Challenges Facing 3-D Audio Display Design for Multimedia", Journal of the Acoustical Society of America, 1999, 105 (2): 1357.

E.M. Wenzel et al., "Localization using Nonindividualized head-Related Transfer Functions", Journal of the Acoustical Society of Americal, Jul. 1993, pp. 111-123.

W. H. Cooke, et al., "Controlled Breathing Protocols Probe Human Autonomic Cardiovascular Rhythms", American Journal of Physiology, 1998, 274:H 709-H718.

M.V. Pitzalis, et al. "Effect of Respiratory Rate on the Relationship Between RR Interval and Systolic Pressure Fluctuations: A Frequency-Dependent Phenomenon", Cardiovascular Research, 1998, 38:332-339.

L. Bernardi, et al, "Effect of Breathing Rate on Oxygen saturation and Exercise Performance in Chronic Heart Failure", The Lancet, May 2, 1998, 351:1308-1311.

A. Mortala, et al, "Abnormal Awake Respiratory Patterns are Common in Chronic Heart Failure and may Prevent Evaluation of Autonomic Tone by Measures of Heart Rate Variability", Circulation, Jul. 1997, 96:246-251.

M.T. La Rovere, et al, "Baroreflex Sensitivity and Heart-Rate Variability in Prediction of Total Cardiac Mortality after Myocardial Infraction", The Lancet, Feb. 14, 1998, 351:478-484.

"Photoplethysmography", 6 pages. 2000. (http://www.lboro.ac.uk/departments/el/research/optics/ppgraphy/ppgmain.htm).

M. Busch, "Respiration: What Pilots Need to Know (But Aren't Taught)" Avweb, 1999, 7 pages. (http://www.avweb.com/articles/respirat.html).

P. Gimondo and P.Mirk, "A New Method for Evaluating Small Intestinal Motility Using Duplex Doppler Sonography", AJR American Journal of Roentgenology, Jan. 1997, 168 (1): 187-192.

An Office Action dated Dec. 3, 2009, which issued during the prosecution of Applicant's Japanese Patent Application No. 2004-527269.

Japanese Patent Laid Open Application No. H07-204238, Aug. 1995. (Including a computer translation).

Japanese Patent Laid Open Application No. 2001-190677, Jul. 2001. (Including a computer translation).

Japanese Patent Laid Open Application No. H10-286292, Oct. 1998. (Including a computer translation).

Japanese Patent Laid Open Application No. 2000-503863.

An Office Action dated Sep. 24, 2012, which issued during the prosecution of U.S. Appl. No. 11/958,083.

An Office Action dated Dec. 28, 2012, which issued during the prosecution of U.S. Appl. No. 13/471,582.

An Office Action dated Jun. 24, 2011, which issued during the prosecution of U.S. Appl. No. 12/427,183.

An Office Action dated Aug. 2, 2011 which issued during the prosecution of Canadian Patent Application No. 2,494,819.

A Supplementary European Search Report dated Nov. 2, 2010, which issued during the prosecution of Applicant's European Patent Application No. EP03784453.

A Translation of an Office Action dated Jan. 26, 2011, which issued during the prosecution of Applicant's Japanese Patent Application No. JP 2007-522123.

A Translation of an Office Action dated Oct. 21, 2010, which issued during the prosecution of Applicant's Japanese Patent Application No. JP 2004-527269.

Nishida et al, "A non-invasive and unreatreined monitoring of human respirstory system by sensorized environment", Proc of the IEEE Sensors 2002, Orlando, FL, Jun. 12-14, 2002.

* cited by examiner

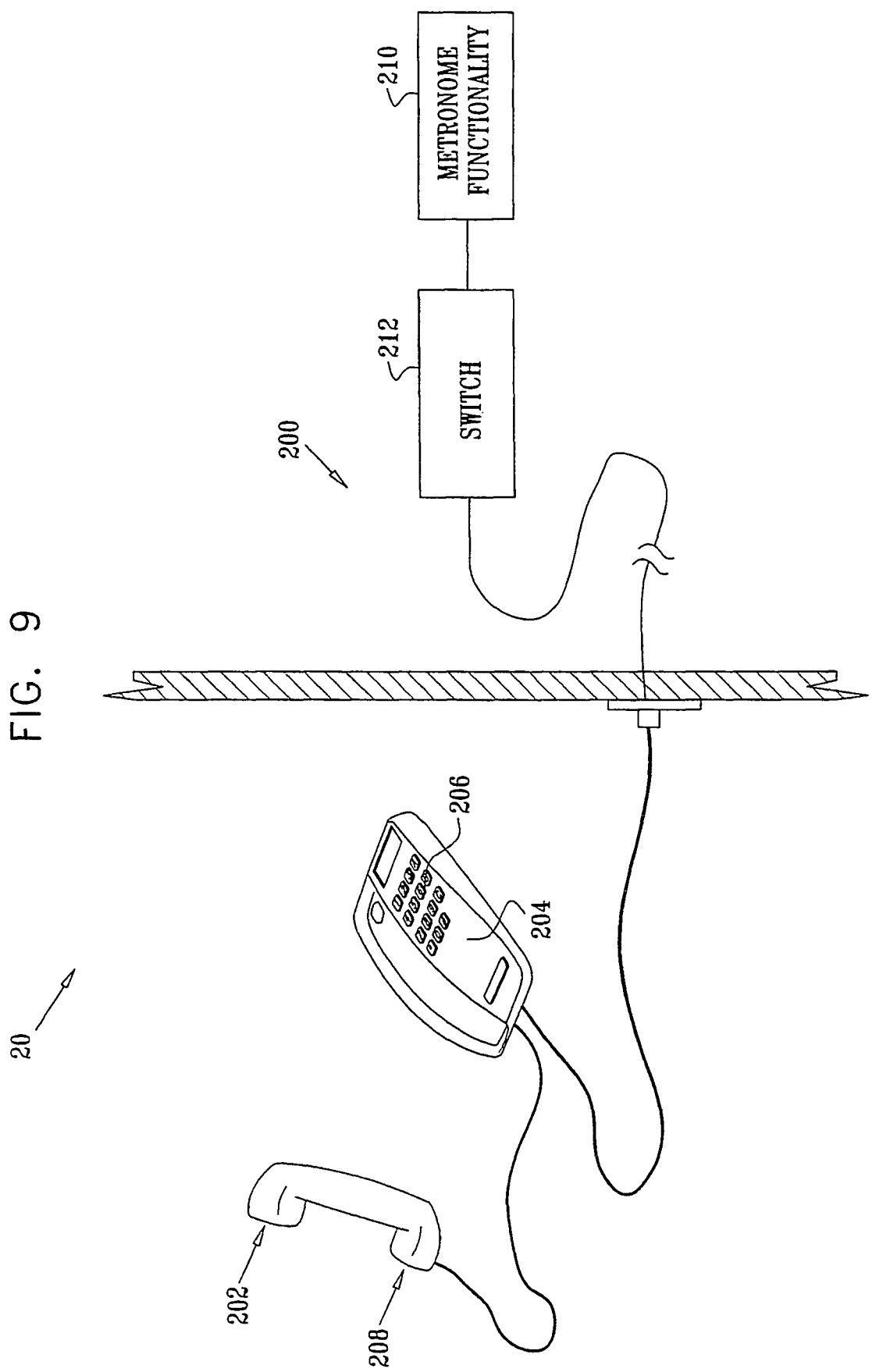

GENERALIZED METRONOME FOR MODIFICATION OF BIORHYTHMIC ACTIVITY

CROSS-REFERENCES TO RELATED APPLICATIONS

The present patent application claims the benefit of U.S. Provisional Patent Application 60/402,378 to Gavish, filed Aug. 9, 2002, entitled, "Generalized metronome for modification of biorhythmic activity," which is assigned to the assignee of the present patent application and is incorporated herein by reference.

FIELD OF THE INVENTION

The present invention relates generally to medical devices, and specifically to exercise devices that modify biorhythmic activity of a user.

BACKGROUND OF THE INVENTION

Physical exercise often involves modifying a multi-phased biorhythmic activity, such as breathing. In a number of cardiovascular diseases, including congestive heart failure (CHF), and pulmonary diseases, including chronic obstructive pulmonary disease (COPD), breathing patterns display irregularities. These irregularities are known markers for disease-related mortality and morbidity. Typical irregularities include Cheyne-Stokes breathing (recurrent episodes of central apnea alternating with hyperpnea), amplitude-modulated breathing (periodic breathing) at a rate of about one modulation per minute, repeated sighs, and breathing at random amplitudes and periods. A reduction in breathing pattern irregularity indicates an improvement in health. The impairment of cardiovascular reflexes, which control blood pressure and volume in an attempt to minimize fluctuations in blood supply to organs (homeostasis), is also clinically significance in cardiovascular and psychosomatic diseases.

U.S. Pat. Nos. 5,076,281, 5,800,337, and 6,099,037 to Gavish, which are incorporated herein by reference, describe methods and devices for modifying biorhythmic activity by measuring one or more variables of a user. The patents describe the generation of a stimulus, which is provided to the user, so as to change the biorhythmic activity of the user in a way that is related in a predetermined way to the monitored biorhythmic activity.

U.S. Pat. No. 5,423,328 to Gavish, which is incorporated herein by reference, describes a stress-detecting device for monitoring respiration, and, in particular, a method for detecting and monitoring circumferential changes in the chest or abdomen of a user resulting from breathing. U.S. Pat. No. 4,580,574 to Gavish, which is incorporated herein by reference, describes a method for non-invasively monitoring properties of living tissue.

U.S. Pat. No. 6,090,037 to Gavish, which is incorporated herein by reference, describes techniques for modification of rhythmic body activity of a user by monitoring biorhythmic activity of the user, and providing the user with a stimulus pattern that resembles but differs from the monitored biorhythmic activity in a way that when followed voluntarily by the user drives a change in the biorhythmic activity.

PCT Publication WO 01/02049 to Gavish et al., which is incorporated herein by reference, describes techniques for facilitating improving health of a user, including a first sensor, adapted to measure a first physiological variable, which is indicative of a voluntary action of the user, a second sensor, adapted to measure a second physiological variable, which is not entirely under the direct voluntary control of the user, and circuitry, adapted to receive respective first and second sensor signals from the first and second sensors, and responsive thereto, to generate an output signal which directs the user to modify a parameter of the voluntary action. The '049 publication also describes an interventive-diagnostic system comprising a local computing device at a local site, which applies an intervention to a user at the site and receives, from one or more sensors attached to the user, one or more input signals indicative of a physiological condition of the user. One embodiment described includes monitoring breathing movements using one sensor, and guiding the user to modify a breathing pattern in an attempt to optimize blood oxygenation, as measured by a second sensor.

U.S. Pat. No. 4,195,626 to Schweizer, which is incorporated herein by reference, describes a biofeedback chamber for applying audible, visual electrical or tactile stimuli to a subject according to a rhythmic pattern. The subject's reactions are measured, analyzed and used to control the stimuli.

U.S. Pat. No. 5,678,571 to Brown, which is incorporated herein by reference, describes a method for treating a medical condition in a patient comprising choosing a psychological strategy for treating the medical condition, and then encoding electronic instructions for an interactive video game. The game implements the psychological strategy, and loads the electronic instructions into a microprocessor-based unit equipped with a display for displaying the video game. The game contains scoring instructions to quantitatively analyze the medical condition of the patient, counseling instructions, and self-care instructions. The video game can be used in conjunction with a physiological variable measuring device connected to the microprocessor-based unit.

U.S. Pat. No. 5,596,994 to Bro, which is incorporated herein by reference, describes an automated and interactive positive motivation system that allows a physician, counselor or trainer to produce and send a series of motivational messages and/or questions to a client to change or reinforce a specific behavioral problem.

U.S. Pat. No. 5,590,282 to Clynes and U.S. Pat. No. 4,526,078 to Chadabe, which are incorporated herein by reference, describe techniques for causing a computer to compose music.

U.S. Pat. No. 4,883,067 to Knispel et al., which is incorporated herein by reference, describes a method for translating a subject's electroencephalogram into music, so as to induce and control various psychological and physiological states of the subject.

U.S. Pat. No. 4,798,538 to Yagi, which is incorporated herein by reference, describes an abdominal respiration training system. The state of the abdominal respiration of a person is measured by a sensor attached to the abdominal region, and the detected breath pattern is compared with an ideal breath pattern.

U.S. Pat. No. 5,827,179 to Lichter et al., which is incorporated herein by reference, describes a real-time biological data processing PC card, adapted to input and process biological data from one or more biological data sensors, and to be interchangeable with other real-time biological data processing PC cards.

U.S. Pat. No. 6,001,065 to DeVito, which is incorporated herein by reference, describes techniques for measuring and performing real-time fast fourier transform (FFT) analysis of bioelectrical signals such as electroencephalogram (EEG) and electromyography (EMG) signals for the control of systems. Passive and active interaction with various electronic media such as video games, movies, music, virtual reality, and computer animations is also described.

U.S. Pat. No. 6,561,908 to Hoke, which is incorporated herein by reference, describes a gaming device having a metronome system. The metronome system includes a CPU which reads game state data on ticks determined by a check-back rate. The CPU causes sound file changes to occur any time any tick occurs, thereby enabling a plurality of sound recordings to be interfaced on-beat or otherwise. The invention is described as providing gaming devices with enhanced sound and music capabilities, adding to a gaming device player's enjoyment and entertainment.

U.S. Pat. No. 5,850,048 to Ruf, which is incorporated herein by reference, describes a metronome unit that comprises an electronic metronome, and a keyboard associated with the entry of a musical signature including the number of beats per measure. The unit also comprises timing means to generate an electronic version of the musical signature, a memory for storing information relating to the musical signature, and an electronic controller. The controller stores information representative of the musical signature entered by way of the keyboard, converts the signal generated by the timing means into a visual representation of the musical signature suitable for viewing on the display, and updates the display in accordance with a beats-per-measure aspect of the musical signature so that a user may be visually informed as to the correct beat of the measure. The keyboard may also include a tempo key and a set of numerical keys facilitating the entry of a desired tempo, and one or more tempo preset keys.

U.S. Pat. No. 5,751,825 to Myers et al., which is incorporated herein by reference, describes apparatus comprising headphones combined with an electronic metronome. The headphones comprise two earcups, a first set of transducers housed within each earcup which receive and reproduce electronic audio signals from an exterior source, an electronically actuated metronome circuit used as a tempo device housed within the earcups, a second set of transducers housed within each earcup to produce the audio signals originating from the metronome circuit, and a tempo control switch for increasing and decreasing the time beats originating from the metronome circuit.

U.S. Pat. No. 5,515,764 to Rosen, which is incorporated herein by reference, describes an electronic metronome device producing precisely timed and tuned rhythms and pitches that are pre-programmed to correspond to specific scales or modes, arpeggios, chords, and etudes. A combination of microprocessor and user interface stores these musical exercises and retrieves them from an electronic memory, inputs them to a signal processor for amplification and modification, and outputs them to speakers, optical displays, or audio outputs.

U.S. Pat. No. 5,447,089 to Marrash, which is incorporated herein by reference, describes an electronically-programmable metronome having a footswitch for allowing a user to adjust the tempo over a continuous range without taking hands off an instrument or interrupting playing. The metronome unit includes a display for menu selection, prompts, and visual cues for adjustment of the tempo and selection of types of clicks in a beat pattern. The microcontroller for the metronome unit can be programmed with any combination of time signatures, rhythms, or patterns with desired cues or accents.

U.S. Pat. No. 5,402,188 to Wayne, which is incorporated herein by reference, describes pacing goggles that include a pacing device that conveys a rhythmic or periodic visual signal to a swimmer. The intermittent signal provides a metronome-like reference for use in pacing the swimmer's strokes. The frequency of the intermittent signal can be adjusted to correspond with the swimmer's preferred pace.

U.S. Pat. No. 6,086,379 to Pendergast et al., which is incorporated herein by reference, describes a training system and method used to improve the biomechanics, distance per stroke, and aerobic metabolism of a swimmer. The system employs a computer interface which allows a coach or a swimmer to input a particular training strategy using pace lights and a timing system or, alternatively, using the system's internal training program. The system provides a generator to collect data from a swimmer. The system includes: (a) swim goggles with LEDs to communicate with the swimmer via a flashing signal or the like what part of the swim stroke the swimmer should be in, thereby assisting the swimmer in achieving a particular stroke frequency, and (b) an arrangement of a plurality of computer controlled pace light strips to assist the swimmer in obtaining proper swimming speed.

U.S. Pat. No. 5,921,890 to Miley, which is incorporated herein by reference, describes a programmable pacing device for helping a user to achieve a desired pace or tempo. The device is capable of emitting a plurality of different audible signals, each signal conveying selected pacing information to the user. The device is described as being usable by athletes to help in training or race pacing, or in the medical field for applications such as a walking pace device to assist in a proactive medical regime for example, as treatment for Parkinson's disease, or for other physiological therapy-based activities.

U.S. Pat. No. 5,027,686 to Ishikawa, which is incorporated herein by reference, describes an electronic metronome comprising circuitry for setting a desired tempo, a circuit for generating a tempo signal corresponding in time to the desired tempo, circuitry for setting a desired time period, and a circuit for generating a time-up signal corresponding in time to the end of the desired time period. A sound generator receives the tempo signal and the time-up signal for generating a tempo sound for each tempo signal and a time-up sound for the time-up signal. A control circuit terminates the generation of the tempo sounds after the generation of the time-up sound.

U.S. Pat. No. 4,733,593 to Rothbart, which is incorporated herein by reference, describes a microprocessor-controlled metronome in which the type (strong or weak), pattern (order and number of strong and weak), and frequency of beats are determined by data stored in a memory manually programmable by means of a keyboard or the like and capable of storing information to produce metronome beats of different types, patterns and relative frequencies combined in various sequences to produce metronome passages consisting of one or more of those sequences, the memory being capable of storing a plurality of such passages and to produce beats corresponding thereto on command.

U.S. Pat. No. 5,592,143 to Romney et al., which is incorporated herein by reference, describes a pulsed-tone timing method. Pulsed audible guide tones are activated at an initial pulsing rate. The pulsing rate is manipulated so as to repeatably (i) increase the pulsing rate over a time span to an intermediate pulsing rate and (ii) abruptly drop the pulsing rate to a decreased rate between the intermediate pulsing rate and a previous rate, until a predetermined final pulsing rate is reached. The pulsing rate can be manipulated such that each subsequent intermediate pulsing rate pulses at a faster rate than previous intermediate pulsing rates.

U.S. Pat. No. 6,212,135 to Schreiber, which is incorporated herein by reference, describes a device for assisting an individual participating in a focused breathing session consisting of at least one respiration cycle. The device produces a first sensory cue which corresponds to the exhalation phase of the respiratory cycle and a second sensory cue which corresponds to the inhalation phase of the respiratory cycle. The first and second sensory cues are repeatedly produced by the device at a specific rate over the duration of the focused breathing session as selected by the individual or in accordance with a predetermined program. In one embodiment of the device, the sensory cues are visually produced by a light projecting sphere. In another embodiment, the sensory cues are audible.

U.S. Pat. No. 4,711,585 to Fresquez et al., which is incorporated herein by reference, describes apparatus for providing perceptible cueing signals to an expectant mother to which she may synchronize her breathing for the purpose of easing delivery, including an oscillator of selectable frequency and duty cycle which drives physiologically perceptible transducers.

U.S. Pat. No. 4,583,443 to Senghaas et al., which is incorporated herein by reference, describes an electronic metronome for training musical students in various rhythm patterns.

U.S. Pat. No. 4,974,483 to Luzzatto, which is incorporated herein by reference, describes a programmable electronic metronome, capable of registering all meter and speed characteristics of any musical work and of producing, when the musical work is to be performed, substantially sharp, perceivable, e.g., acoustic, signals representing such characteristics in the appropriate succession.

The following US patents, all of which are incorporated herein by reference, may be of interest:

| | | |
|---|---|---|
| D449,236 | D315,518 | 4,090,355 |
| 6,201,769 | 4,982,642 | 4,070,944 |
| 6,179,723 | 4,759,253 | 4,018,131 |
| D430,810 | D295,728 | 4,014,167 |
| D430,045 | 4,649,794 | 4,012,901 |
| 6,015,948 | 4,629,331 | 3,996,833 |
| D389,080 | 4,612,841 | 3,945,292 |
| D388,340 | 4,602,551 | 3,942,404 |
| D378,899 | 4,462,297 | 6,407,324 |
| 5,586,088 | 4,442,752 | 5,959,230 |
| D368,949 | 4,380,185 | 5,453,567 |
| D360,144 | 4,354,412 | 5,195,061 |
| D360,143 | 4,333,172 | 4,366,741 |
| 5,417,137 | 4,237,549 | 4,321,853 |
| D351,800 | 4,218,874 | 4,213,093 |
| D343,186 | 4,204,400 | 4,173,168 |
| 5,214,228 | 4,193,257 | 4,163,409 |
| D323,469 | D253,399 | 4,082,029 |
| D319,791 | D249,936 | 3,991,648 |

The following articles, all of which are incorporated herein by reference, may be of interest:

Cooke et al., "Controlled breathing protocols probe human autonomic cardiovascular rhythms," American Journal of Physiology 274:H709-H718 (1998)

Pitzalis et al., "Effect of respiratory rate on the relationship between RR interval and systolic blood pressure fluctuations: a frequency-dependent phenomenon," Cardiovascular Research 38:332-339 (1998)

Bernardi et al., "Effect of breathing rate on oxygen saturation and exercise performance in chronic heart failure," The Lancet 351:1308-1311 (1998)

Mortara et al., "Abnormal awake respiratory patterns are common in chronic heart failure and may prevent evaluation of autonomic tone by measures of heart rate variability," Circulation 96:246-252 (1997)

La Rovere et al., "Baroreflex sensitivity and heart-rate variability in prediction of total cardiac mortality after myocardial infarction," The Lancet 351:478484 (1998)

Gimondo et al., "A new method for evaluating small intestinal motility using duplex Doppler sonography," AJR American Journal of Roentgenology 168(1):187-192 (1997)

SUMMARY OF THE INVENTION

In some embodiments of the present invention, a device for beneficial modification of biorhythmic activity of a user comprises a metronome adapted to generate and dynamically modify a multi-phase rhythmic output signal. Typically, the biorhythmic activity includes respiration, and the device configures the output signal so as to direct the user to modify one or more timing parameters of the respiration. The device typically does not comprise any physiological sensors. Alternatively, the device does comprise a physiological sensor (e.g., a respiration sensor), but the device receives data from the sensor prior to directing the user to modify the timing parameters, and not substantially throughout generation and modification of the output signal.

The output signal typically comprises an intelligible stimulus, such as a sound pattern and/or a dynamic graphical pattern. The stimulus is typically intended to modify respiration of the user by training the user to initiate a new breathing pattern. For example, the output signal may direct the user to change the timing of inspiration and expiration so as to cause a reduction in a ratio of inspiration to expiration. For some interventions, it is desirable to reduce this ratio, for example towards 1:4, from a pre-intervention level generally of 1:1 or 1:2. For some interventions, the new breathing pattern includes additional phases not generally included in normal, undirected breathing patterns. For example, normal breathing generally includes two phases, inspiration and expiration. The device may configure the output signal to direct the user to add the phases of breath holding and/or post-expiratory pausing.

During a typical session of use, the user selects a stored exercise pattern, and activates the device to generate the output signals responsive to the pattern. The user typically uses the device during multiple sessions that extend over a period of time, generally days, months or years. Each session typically has a length of between about 10 and about 20 minutes, most typically about 15 minutes. The user typically configures the device to gradually modify exercise patterns over the period of time, which generally facilitates adaptation of cardiovascular, pulmonary, and neural systems to the dynamic changes developed by the exercise. Use of the device often results in a substantial increase in adherence to a routine schedule of exercise performance. Without the device, subjects in need of breathing exercise generally do not adequately adhere to a routine schedule of exercise performance, for example because of boredom or lack of personal discipline.

Routine use of the device may increase the degree of voluntary control a user has over a disease-related breathing irregularity, such as those described in the Background of the Invention. Such routine use may thus be beneficial for reducing mortality and morbidity related to some medical conditions. For example, the use of the device may be beneficial for treating the following conditions:

some cardiovascular diseases, including congestive heart failure (CHF);

some pulmonary diseases, including chronic obstructive pulmonary disease (COPD);
some neurological diseases, such as panic disorder;
hypertension; and
hyperactivity, such as in children.

Techniques described herein may be used in conjunction with techniques described in (a) U.S. patent application Ser. No. 09/611,304, filed Jul. 6, 2000, entitled, "Interventive-diagnostic device," (b) PCT Publication WO 01/02049 to Gavish et al., and/or (c) U.S. patent application Ser. No. 10/323,596 to Gavish, filed Dec. 13, 2002, all of which are assigned to the assignee of the present patent application and are incorporated herein by reference. Alternatively or additionally, techniques described herein may be used in conjunction with techniques described in one or more of the references cited in the Background section of the present patent application.

Although the user of the device, i.e., the person whose biorhythmic activity the device is modifying, is sometimes described herein as programming and/or configuring the device, such programming and/or configuring may also be performed by a person other than the user, e.g., a healthcare worker or exercise instructor, who, for example, configures and/or programs the device either through the device user interface or remotely over a telephone or network connection.

There is therefore provided, in accordance with an embodiment of the present invention, apparatus for use with a subject, including:
a memory, storing a set of computer instructions,
wherein the memory is adapted to have stored therein an initial form of a multi-phase biorhythmic activity pattern and an indication of a desired form of the multi-phase biorhythmic activity pattern,
wherein a ratio of durations of two phases in the desired form is different from a ratio of durations of the respective phases in the initial form, and
wherein at least one phase of the multi-phase biorhythmic activity pattern corresponds to a respective phase of a multi-phase biorhythmic activity of the subject; and
a stimulus unit, adapted to execute the stored instructions and to generate responsive thereto a time-varying stimulus that: (a) is substantially not responsive to ongoing measurement of the multi-phase biorhythmic activity during generation of the time-varying stimulus, and (b) has a multi-phase pattern that is characterized by a series of transitional forms intermediate the initial form and the desired form that guide the subject to modify the biorhythmic activity.

For some applications, the stimulus unit is adapted to generate the time-varying stimulus having the multi-phase pattern, and durations of the transitional forms in the series vary linearly over time. Alternatively, the stimulus unit is adapted to generate the time-varying stimulus having the multi-phase pattern, and durations of the transitional forms in the series vary geometrically over time.

In an embodiment, the initial form has a first number of phases and the desired form has a second number of phases, the first number not equal to the second number, and the memory is adapted to have stored therein the initial form and the indication of the desired form having the differing numbers of phases.

In an embodiment, the initial form has a greater number of phases than the desired form, and the memory is adapted to represent a phase that is in the initial form but not in the desired form by setting a duration thereof equal to zero in the desired form. Alternatively, the desired form has a greater number of phases than the initial form, and the memory is adapted to represent a phase that is in the desired form but is not in the initial form by setting a duration thereof equal to zero in the initial form. Further alternatively, the initial form and the desired form have the same number of phases, and the memory is adapted to have stored therein the initial form and the indication of the desired form having the same number of phases.

In an embodiment, the memory is adapted to have stored therein the initial form and the indication of the desired form prior to use of the apparatus with the subject.

In an embodiment, the time-varying stimulus includes at least one stimulus selected from the list consisting of: an image, alpha-numeric text, a sound, a sound pattern, a dynamic graphical pattern, and a visual cue, and the stimulus unit includes a visual stimulator, adapted to generate the selected time-varying stimulus. In an embodiment, the time-varying stimulus includes pressure, and the stimulus unit includes a pressure applicator, adapted to apply the pressure to a portion of a body of the subject. In an embodiment, the time-varying stimulus includes massage, and the stimulus unit includes a massaging device, adapted to massage a portion of a body of the subject. In an embodiment, the time-varying stimulus includes mechanical energy, and the stimulus unit includes a mechanical stimulator, adapted to apply the mechanical energy to a portion of a body of the subject. In an embodiment, the time-varying stimulus includes an electrical current, and the stimulus unit includes an electrical stimulator, adapted to apply the current to a portion of a body of the subject. In an embodiment, the time-varying stimulus is in the form of a game, and the stimulus unit includes a game generator, adapted to alter parameters of the game so as to guide the subject to modify the multi-phase biorhythmic activity.

For some applications, the stimulus unit is adapted to transmit the time-varying stimulus over a telephone network to the subject. Alternatively, the stimulus unit is adapted to transmit the time-varying stimulus over a wide-area network to the subject.

In an embodiment, the apparatus includes a muscle stimulator, adapted to operate in conjunction with the stimulus unit and to apply to a muscle of the subject an electrical current configured to stimulate the muscle.

In an embodiment, the stimulus unit is adapted to configure the time-varying stimulus to increase tissue oxygenation of the subject, to increase mechanical compliance of blood vessels of the subject, to reduce peripheral impedance of small blood vessels of the subject, to increase heart rate variability of the subject, and/or to increase baroreflex sensitivity of the subject.

In an embodiment, the apparatus includes a motion stimulator, adapted to operate in conjunction with the stimulus unit and to generate a motion stimulus that guides the subject to perform movements of a limb of a body of the subject.

For some applications, the stimulus unit is adapted to generate the time-varying stimulus when the subject is sleeping. For some applications, the stimulus unit is adapted to generate the time-varying stimulus when the subject is mechanically ventilated.

In an embodiment, the time-varying stimulus includes music. For some applications, the stimulus unit includes a music synthesizer, adapted to generate the music.

In an embodiment, the stimulus unit is adapted to generate a time-varying stimulus that is substantially not responsive to ongoing measurement of a physiological variable of the subject during generation of the time-varying stimulus. In an embodiment, the stimulus unit is adapted to generate a time-varying stimulus that is not responsive to a measurement of a physiological variable of the subject during use of the apparatus with the subject.

In an embodiment, the apparatus includes a sensor, adapted to sense a physiological event and to generate an event signal responsive thereto, the apparatus is adapted to receive the event signal prior to generation of the time-varying stimulus by the stimulus unit, and the stimulus unit is adapted to commence generating the time-varying stimulus responsive to the event signal. For some applications, the apparatus is adapted to configure the initial form at least in part responsively to a parameter of the event signal. In an embodiment, the physiological event includes an episode of sleep apnea, and the sensor is adapted to sense the episode of sleep apnea.

In an embodiment, the memory is adapted to have stored therein a plurality of exercise routines having respective initial forms and respective indications of desired forms, the stimulus unit includes a user interface, adapted to enable the subject to select one of the exercise routines, and the stimulus unit is adapted to generate the time-varying stimulus responsive to the selection. For some applications, the user interface includes a telephone. Alternatively, the user interface includes a user interface of an audio-playback device. Further alternatively, the user interface includes a user interface of a general-purpose computer.

In an embodiment, the stimulus unit is adapted to generate the time-varying stimulus when the subject is unconscious. For some applications, the stimulus unit is adapted to generate the time-varying stimulus when the subject is in a coma. For other applications, the stimulus unit is adapted to generate the time-varying stimulus when the subject is anesthetized.

In an embodiment, the multi-phase biorhythmic activity includes respiration of the subject, and the stimulus unit is adapted to configure the time-varying stimulus to guide the subject to modify the respiration. In an embodiment, the multi-phase biorhythmic activity of the subject is characterized by a rate of breathing, and the memory is adapted to have stored therein the initial form and the indication of the desired form, and a rate of breathing in the desired form is different from a rate of breathing in the initial form.

For some applications, two or more phases in the desired form include at least one respiration phase not generally included in the multi-phase biorhythmic activity prior to generating the time-varying stimulus, and the memory is adapted to have stored therein an indication of the at least one respiration phase.

For some applications, two or more phases in the desired form include at least one respiration phase selected from the list consisting of: breath holding and post-expiratory pausing, and the memory is adapted to have stored therein an indication of the selected respiration phase.

For some applications, the apparatus includes a resistive load, adapted to be applied to the subject and to resist airflow of the subject during a phase of respiration selected from inspiration and expiration. For some applications, the apparatus includes a mechanical ventilator, adapted to be applied to the subject and to operate in conjunction with the stimulus unit.

In an embodiment, two or more phases in the initial and the desired forms include inspiration and expiration, and the memory is adapted to have stored therein the initial form and the indication, and a ratio of a duration of the inspiration to a duration of the expiration (an I:E ratio) in the desired form is less than an I:E ratio in the initial form. For some applications, the memory is adapted to have stored therein the initial form and the indication, and the I:E ratio in the desired form is between about 1:0.5 and 1:4.

In an embodiment, the apparatus includes a user interface, adapted to receive input from the subject, and the apparatus is adapted to store the initial form and the indication of the desired form in the memory, responsive to the input. For some applications, the user interface is adapted to receive an indication of durations of two or more phases in the indication of the desired form.

For some applications, the user interface is adapted to receive indications of trends over time of respective durations of two or more phases in the initial form.

For some applications, the user interface is adapted to receive an indication of durations of two or more phases in the initial form. Alternatively or additionally, the user interface is adapted to receive an indication of durations of two or more phases in the desired form.

In an embodiment, the user interface is adapted to measure a lapse between a start indication and an end indication of at least one of the phases in the indication of the initial form. For some applications, the start and end indications include respective audible indications of respiration of the subject, and the user interface is adapted to sense the audible start and end indications. For some applications, the user interface is adapted to receive the start and end indications from the subject at respective times, and to measure the lapse responsive thereto.

There is also provided, in accordance with an embodiment of the present invention, a method for use with a subject, including:

storing an initial form of a multi-phase biorhythmic activity pattern and an indication of a desired form of the multi-phase biorhythmic activity pattern,
  wherein a ratio of durations of two phases in the desired form is different from a ratio of durations of the respective phases in the initial form, and
  wherein at least one phase of the multi-phase biorhythmic activity pattern corresponds to a respective phase of a multi-phase biorhythmic activity of the subject; and
generating a time-varying stimulus that: (a) is substantially not responsive to ongoing measurement of the multi-phase biorhythmic activity during generation of the time-varying stimulus, and (b) has a multi-phase pattern that is characterized by a series of transitional forms intermediate the initial form and the desired form that guide the subject to modify the multi-phase biorhythmic activity.

There is further provided, in accordance with an embodiment of the present invention, a computer software product including a computer-readable medium, in which program instructions are stored, which instructions, when read by a computer, cause the computer to generate a time-varying stimulus that: (a) is substantially not responsive to ongoing measurement of a multi-phase biorhythmic activity of a subject during generation of the time-varying stimulus, and (b) has a multi-phase pattern that is characterized by a series of transitional forms intermediate an initial form of a multi-phase biorhythmic activity pattern and an indication of a desired form of the multi-phase biorhythmic activity pattern that guide the subject to modify the multi-phase biorhythmic activity,
  wherein at least one phase of the multi-phase biorhythmic activity pattern of the time-varying stimulus corresponds to a respective phase of the multi-phase biorhythmic activity, and
  wherein a ratio of durations of two phases in the desired form is different from a ratio of durations of the respective phases in the initial form.

There is still further provided, in accordance with an embodiment of the present invention, a data storage medium including an arrangement of data corresponding to an output stimulus for guiding a subject to modify a multi-phase biorhythmic activity of the subject, the stimulus including a time-varying multi-phase pattern that is characterized by a series of transitional forms, intermediate an initial form of a multi-phase biorhythmic activity pattern and a desired form of the multi-phase biorhythmic activity pattern, wherein at least one phase of the time-varying multi-phase pattern corresponds to a respective phase of the multi-phase biorhythmic activity, and wherein a ratio of durations of two phases in the desired form is different from a ratio of durations of the respective phases in the initial form.

For some applications, the output stimulus includes music. For some applications, the output stimulus includes at least one stimulus selected from the list consisting of: an image, alpha-numeric text, a sound, a sound pattern, a dynamic graphical pattern, and a visual cue. For some applications, the output stimulus includes pressure for application to a portion of a body of the subject. For some applications, the output stimulus includes massage for application to a portion of a body of the subject. For some applications, the output stimulus includes mechanical energy for application to a portion of a body of the subject. For some applications, the output stimulus includes electrical energy for application to a portion of a body of the subject.

There is yet further provided, in accordance with an embodiment of the present invention, apparatus for use with a subject, including:

a data storage medium including a plurality of arrangements of data, each arrangement corresponding to an output stimulus for guiding the subject to modify a multi-phase biorhythmic activity of the subject, the stimulus including a time-varying multi-phase pattern that is characterized by a series of transitional forms, intermediate an initial form of a multi-phase biorhythmic activity pattern and a desired form of the multi-phase biorhythmic activity pattern, wherein at least one phase of the time-varying multi-phase pattern corresponds to a respective phase of the multi-phase biorhythmic activity, and wherein a ratio of durations of two phases in the desired form is different from a ratio of durations of the respective phases in the initial form; and a stimulus unit, adapted to generate the output stimulus corresponding to a selected arrangement.

The present invention will be more fully understood from the following detailed description of embodiments thereof, taken together with the drawings, in which:

BRIEF DESCRIPTION OF THE DRAWINGS

FIG. 9 is a schematic illustration of an implementation of the metronome of FIG. 1 over a telephone network, in accordance with an embodiment of the present invention.

DETAILED DESCRIPTION OF EMBODIMENTS

Figure 1:
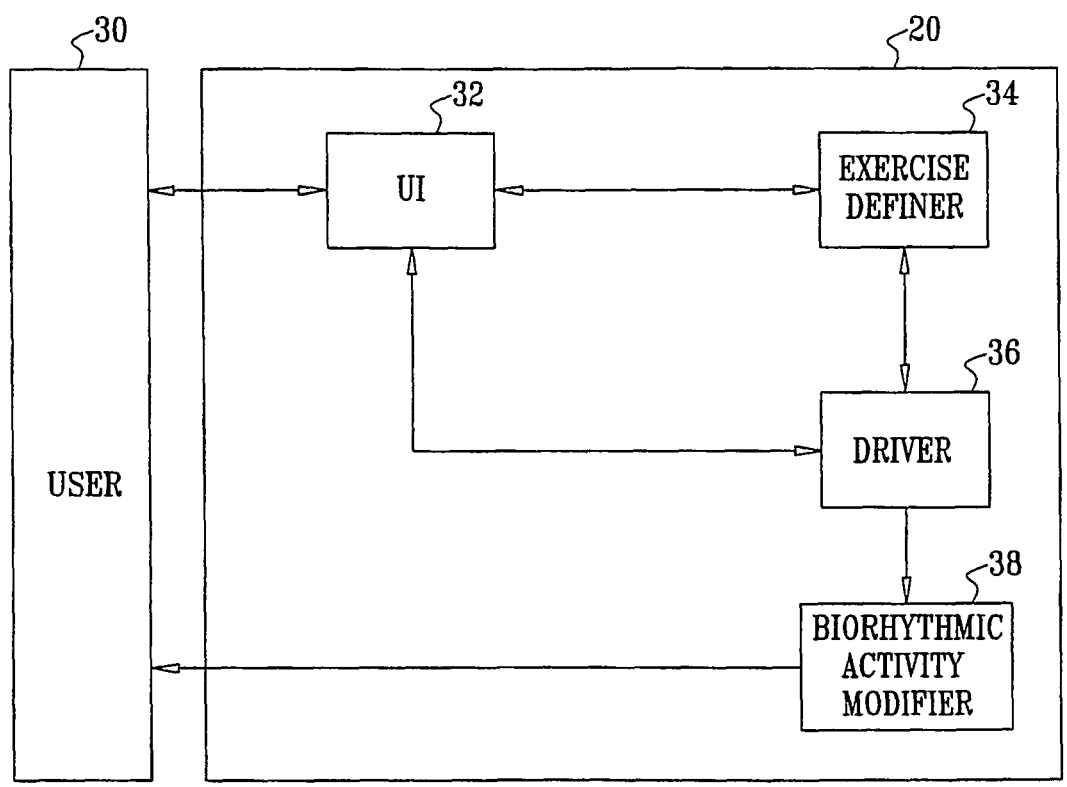
FIG. 1 is a schematic block diagram showing components of a dynamic metronome for beneficial modification of biorhythmic activity of a user, in accordance with an embodiment of the present invention.

FIG. 1 is a schematic block diagram showing components of a dynamic metronome 20 for beneficial modification of biorhythmic activity of a user 30, in accordance with an embodiment of the present invention. Metronome 20 comprises a user interface (UI) 32, an exercise definer 34, a driver 36, and a biorhythmic activity modifier 38. Exercise definer 34 enables the user to define a new exercise routine, as described hereinbelow with reference to FIG. 6, or edit an existing routine. When the user activates metronome 20 to execute an exercise routine, driver 36 creates an exercise pattern file based on the selected exercise routine, as described hereinbelow with reference to FIG. 7. Alternatively, driver 36 retrieves an exercise pattern file that was previously created and stored. Based on the exercise pattern file, driver 36 generates a temporal sequence of data, and uses the sequence to drive biorhythmic activity modifier 38 to generate output signals to the user, as described hereinbelow with reference to FIG. 8, so as to modify the biorhythmic activity.

The output signals are typically intended to modify respiration of user 30, by training the user to initiate a new breathing pattern. For example, the output signals may direct the user to change the timing of inspiration and expiration so as to cause a reduction in a ratio of inspiration to expiration (I:E ratio). For some interventions, it is desirable to reduce the I:E ratio, for example towards 1:4, from a pre-intervention level generally of 1:1 or 1:2. For some interventions, the new breathing pattern includes additional phases not generally included in normal, undirected breathing patterns. For example, normal breathing generally includes two phases, inspiration and expiration. Metronome 20 may configure the output signals to direct user 30 to add the phases of breath holding and/or post-expiratory pausing.

Figure 2:
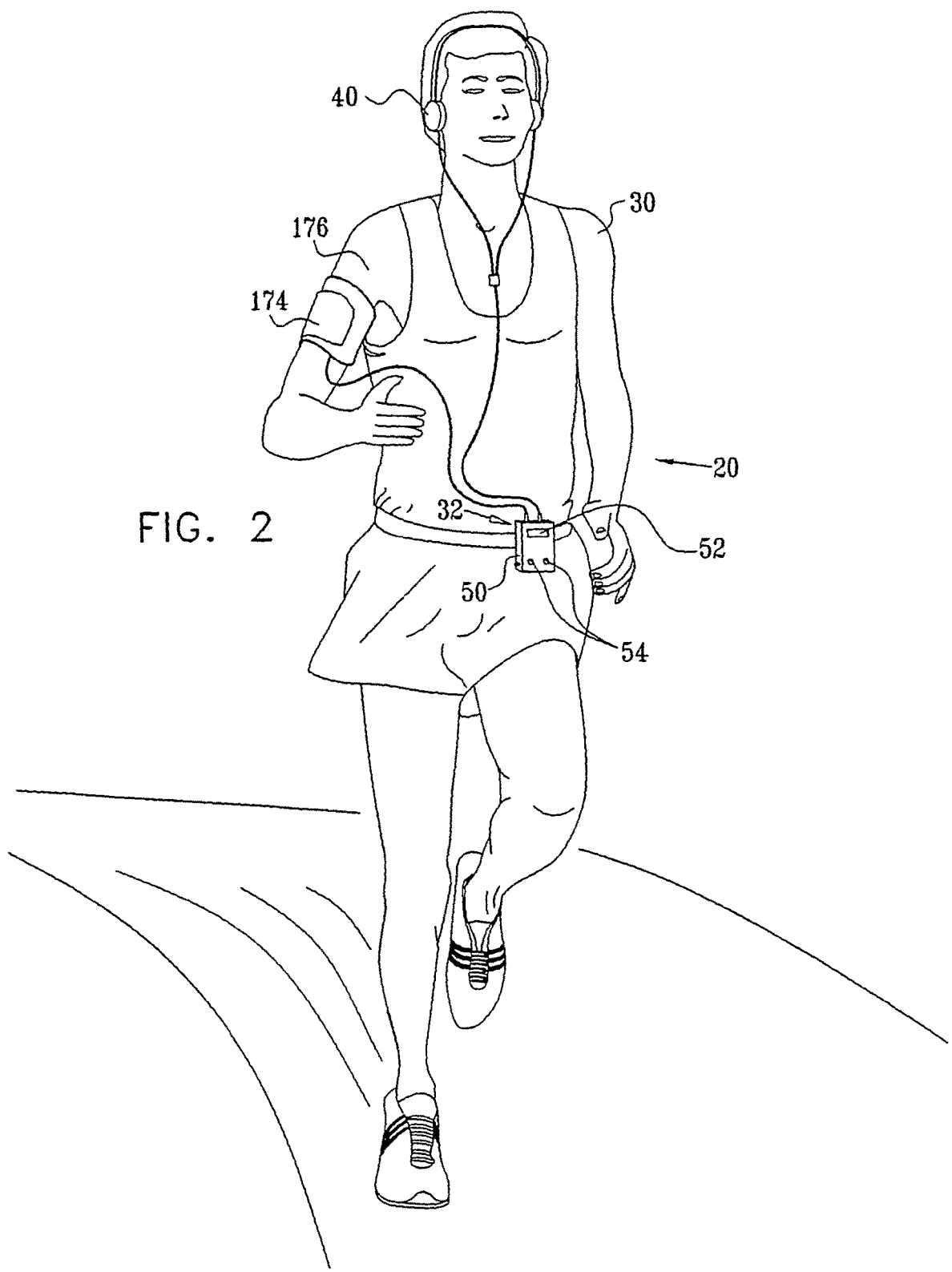
FIG. 2 is a schematic pictorial illustration of an implementation of the metronome of FIG. 1 as a dedicated standalone device, in accordance with an embodiment of the present invention.

FIG. 2 is a schematic pictorial illustration of an implementation of metronome 20 as a dedicated standalone device 50, in accordance with an embodiment of the present invention. For some applications, standalone device 50 is portable and/or battery-operated. The standalone device may be implemented in dedicated hardware logic, or using a combination of hardware and software elements. In this embodiment, UI 32 typically comprises a display screen 52 and several input elements 54, such as buttons, keys, or knobs. For example, input elements 54 may comprise on/off, enter, up, down, and setup buttons. For some applications, metronome 20 offers the option of setting default values, such as by using the setup button. For example, the user may set default parameters for the number of phases, as described hereinbelow, or sound volume.

Figure 3:
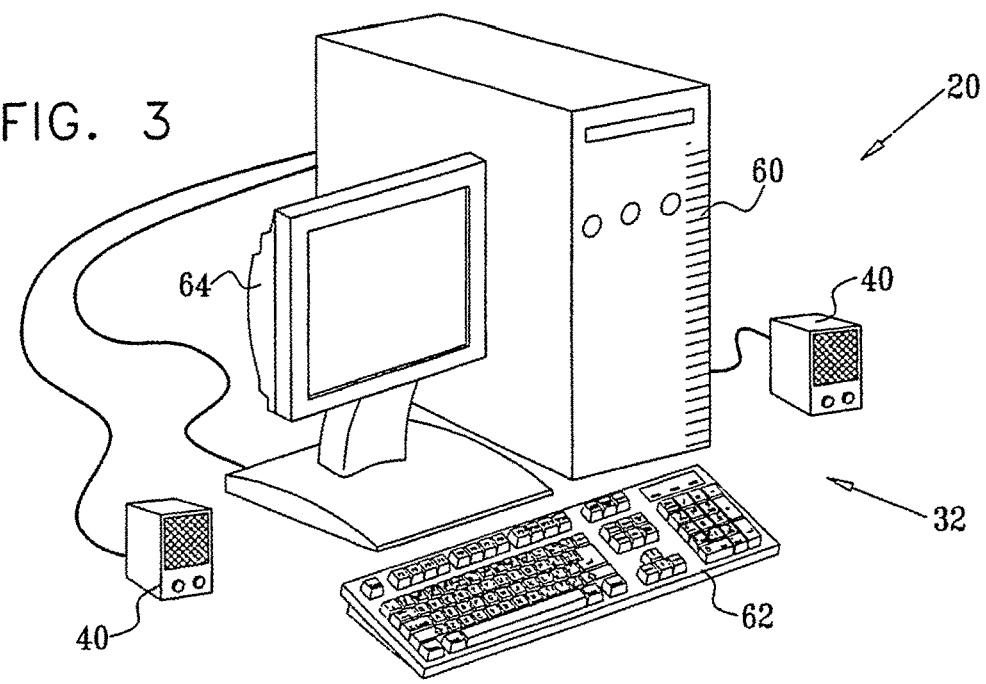
FIG. 3 is a schematic pictorial illustration of an implementation of the metronome of FIG. 1 as software on a general-purpose computer, in accordance with an embodiment of the present invention.

FIG. 3 is a schematic pictorial illustration of an implementation of metronome 20 as software on a general-purpose computer 60, in accordance with an embodiment of the present invention. Computer 60 is programmed in software to carry out the functions described herein. The software may be downloaded to the computer in electronic form, over a network, for example, or it may alternatively be supplied to the computer on tangible media, such as magnetic or optical media or other non-volatile memory, e.g., CD-ROM. In this embodiment, UI 32 typically comprises a keyboard 62 and a monitor 64. For some applications, all or a portion of metronome 20 is implemented as a web service, accessible to user 30 over a wide-area network, typically the Internet. Although general-purpose computer 60 is shown in FIG. 3 as a personal computer, this is by way of illustration and not limitation, and general-purpose computer 60 may comprise other computing devices, such as a handheld computing device.

Figure 4A:
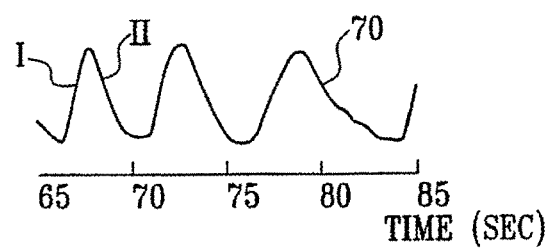
FIGS. 4A, 4B, and 4C are schematic illustrations of several biorhythmic activity signals, in accordance with an embodiment of the present invention.
Figure 4B:
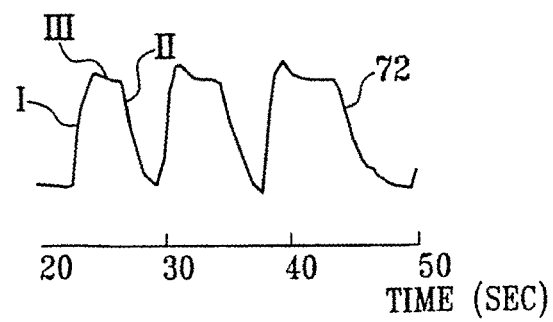
Figure 4C:
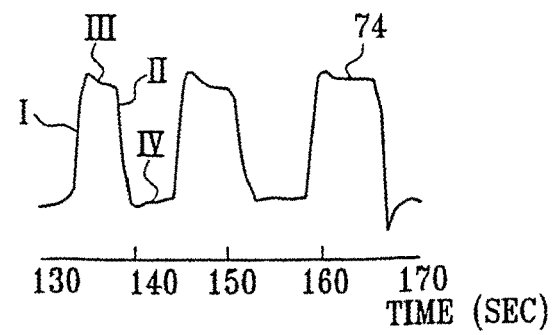

FIGS. 4A, 4B, and 4C are schematic illustrations of several biorhythmic activity signals, in accordance with an embodiment of the present invention. These biorhythmic activity signals represent exemplary chest circumferences of user 30 when metronome 20 is adapted to modify respiration. In FIG. 4A, a line 70 represents an activity signal during a two-phase breathing exercise. Inspiration occurs during phase I, and expiration during phase II. In FIG. 4B, a line 72 represents an activity signal during a three-phase breathing exercise. In addition to inspiration and expiration, the exercise includes breath holding during phase III. In FIG. 4C, a line 74 represents an activity signal during a four-phase breathing exercise. This activity signal additionally includes phase IV, during which post-expiratory pausing occurs. As used herein, a "biorhythmic pattern" comprises two or more phases, and "biorhythmic activity" comprises a sequence of biorhythmic patterns.

Figure 5:
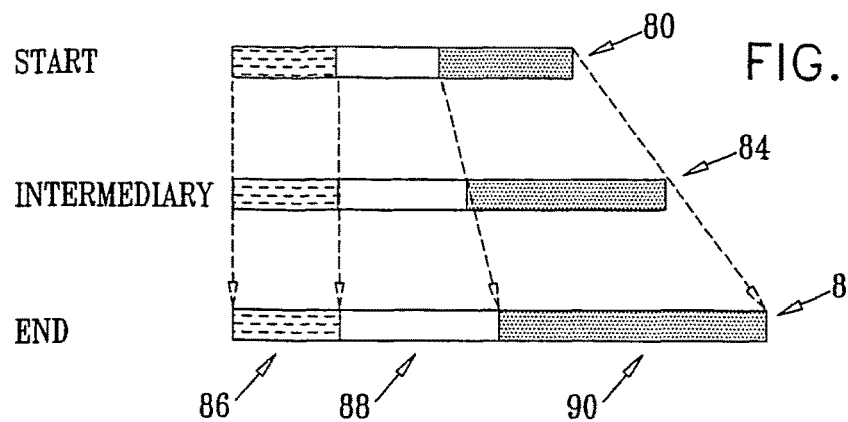
FIG. 5 is a schematic illustration showing a transformation of a biorhythmic pattern during a breathing exercise, in accordance with an embodiment of the present invention.

FIG. 5 is a schematic illustration showing a transformation of a biorhythmic pattern 80 during a breathing exercise, in accordance with an embodiment of the present invention. Metronome 20 is adapted to generate and dynamically modify a multi-phase rhythmic output signal, so as to direct user 30 to gradually modify start biorhythmic pattern 80 to a desired end biorhythmic pattern 82, through at least one intermediary biorhythmic pattern 84. In the exemplary transformation shown in FIG. 5, the biorhythmic patterns include three phases 86, 88, and 90. For some interventions, metronome 20 directs user 30 to modify the phases by different amounts, and/or to modify only a portion of the phases. In the example shown in the figure, the metronome directs the user to maintain the initial duration of phase 86, increase the duration of phase 88 by a first amount, and to increase the duration of phase 90 by a second amount, greater than the first amount.

For some applications, the number of phases of start biorhythmic pattern 80, intermediary biorhythmic pattern 84, and/or end biorhythmic pattern 82 is greater or less than the number of phases of the user's natural biorhythmic pattern. For example, the user's natural biorhythmic pattern may have four phases, while start biorhythmic pattern 80, intermediary biorhythmic pattern 84, and/or end biorhythmic pattern 82 has only two phases. Alternatively or additionally, two or more phases of start biorhythmic pattern 80, intermediary biorhythmic pattern 84, and/or end biorhythmic pattern 82 correspond to a single phase of the user's natural biorhythmic pattern. For example, start biorhythmic pattern 80, intermediary biorhythmic pattern 84, and/or end biorhythmic pattern 82 may comprise two sub-phases of inspiration that correspond to a single phase of inspiration of the user's natural biorhythmic pattern.

In an embodiment of the present invention, when user 30 turns on metronome 20, the metronome gives the user the option to either define a new exercise routine or choose a routine from a stored library. Typically, if the user makes no selection within a predetermined period, e.g., one minute, metronome 20 automatically powers down.

Figure 6:
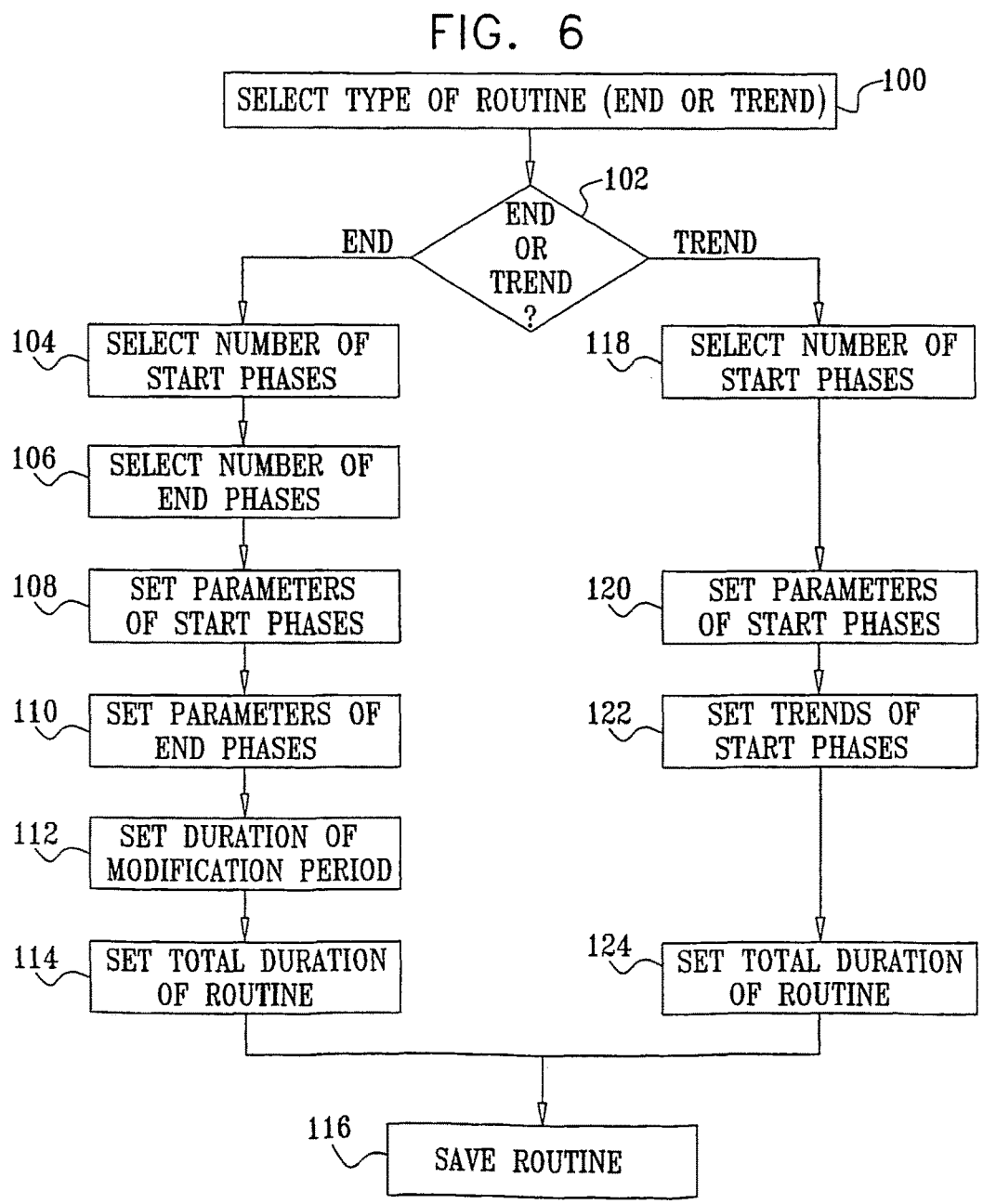
FIG. 6 is a flow chart illustrating a method for defining a new exercise routine, in accordance with an embodiment of the present invention.

FIG. 6 is a flow chart illustrating a method for defining a new exercise routine, in accordance with an embodiment of the present invention. To begin defining the new exercise routine, user 30 selects whether the routine is of an "end" type or a "trend" type, at a type selection step 100. "End" type routines allow the user to define the parameters of the start and end biorhythmic patterns, as described hereinbelow, while "trend" type routines allow the user to define the parameters of the start biorhythmic pattern and trends of each of the phases of the start biorhythmic pattern, as described hereinbelow. User 30 makes this selection, as well as other selections, using UI 32, for example using up and down buttons for scrolling through options, and an enter button for making a selection.

At an end/trend check step 102, metronome 20 checks which type of routine user 30 selected. If the user selected an "end" type routine, metronome 20 prompts the user to enter a desired number of phases of the start biorhythmic pattern, at a start phase number selection step 104. The metronome also prompts the user to enter a desired number of phases of the end biorhythmic pattern, at an end phase number selection step 106. For some applications, metronome 20 does not provide the option of selecting different numbers of phases for the start and end biorhythmic patterns; steps 104 and 106 are therefore combined, to prompt the user to enter a single number of phases for both the start and end biorhythmic patterns.

User 30 sets the parameters of each of the phases of the start biorhythmic pattern, at a start parameters set step 108. The user typically, but not necessarily, attempts to set these parameters based on the user's current spontaneous respiration pattern, i.e., before treatment with the routine currently being defined. (The user could also, for example, arbitrarily set start parameters indicative of timing faster than the user's spontaneous respiration pattern.) For some applications, the user enters a duration (typically in seconds) of each applicable phase using a numerical entry facility of UI 32. The user typically enters zero for phases that do not occur in the user's spontaneous respiration pattern, e.g., breath holding and/or post-expiratory pausing. Alternatively, the user indicates a duration of each applicable phase by indicating in real-time the start and end of each phase (e.g., by pressing one or more buttons) during self-observation of his or her breathing pattern. The metronome measures the lapse between the start and end indications, e.g., using an internal clock, in order to determine the selected duration of the phase. For some applications, metronome 20 produces click sounds during step 108 to help the user define the phase. Further alternatively, UI 32 comprises a microphone, which senses the user's spontaneous respiration pattern, and determines the timing of the phases thereof in real-time. (It is noted that metronome 20 typically performs such sensing of respiration only during definition of exercise routines, and not during use of the metronome for exercise.) Other methods for indicating the start parameters will be evident to one skilled in the art, having read the present patent application.

At an end parameters set step 110, user 30 sets the parameters of each of the phases of the end biorhythmic pattern. For example, the user may determine these parameters based on an instruction manual accompanying metronome 20, the recommendation of a health care provider or exercise instructor, or personal experience using the metronome. Techniques for setting the start parameters, as described with reference to step 108, may be used for setting the end parameters. To use the real-time techniques described, the user briefly exerts voluntary control of his or her respiration to mimic the desired end biorhythmic pattern.

For some applications, at steps 108 and/or 110 the user is given the option of choosing the type of synthesized instrument(s) to be used for each phase during exercise, as described hereinbelow with reference to FIG. 8. Alternatively or additionally, the user is given the option to select which "song," i.e., combination of musical phases, to use during exercise. Such a selection typically may be made either during exercise routine definition, or during use of the metronome for exercise. For some applications, the user uses a setup button to make the selection.

For some applications, while the user is defining the exercise routine at steps 108 and 110, metronome 20 continuously outputs a stimulus indicative of the parameters selected by the user for the phase currently being defined. In order to output the stimulus, metronome 20 activates driver 36 to drive biorhythmic activity modifier 38, as described hereinbelow with reference to FIG. 8. This instantaneous feedback generally helps the user define the parameters.

At a modification period duration set step 112, user 30, using UI 32, sets a duration of the period over which the metronome, during an exercise session using the defined exercise routine, dynamically varies the output signal to drive the transformation from the start biorhythmic pattern to the end biorhythmic pattern. Optionally, the user also sets a total duration of the exercise routine, at a routine duration set step 114. This total duration must be no less than the modification period duration. If the total duration is greater than the modification period duration, the metronome, during an exercise session, after the end biorhythmic pattern has been achieved, maintains the end biorhythmic pattern for a period equal to the difference between the total duration and the modification period.

Metronome 20 then saves the defined exercise routine, at a save routine step 116. Metronome 20 typically offers user 30 the option of immediately launching an exercise session using the newly-defined exercise routine, as described hereinbelow.

If, however, user 30 selected a "trend" type routine at check step 102, the metronome prompts the user to enter a desired number of phases of the start biorhythmic pattern, at a start phase number selection step 118. At a start parameters set step 120, user 30 sets the parameters of each of the phases of the start biorhythmic pattern, using techniques described hereinabove with reference to step 108. Instead of setting parameters of an end biorhythmic pattern, as described hereinabove for "end" type routines, the user sets trends of each of the start phases, at a set trends step 122. For some applications, the trends indicate percentage changes of the respective durations of each of the start phases, e.g., to lengthen each phase by a certain percentage during each respiration cycle or during a given period, e.g., each minute. Optionally, the same percentage change is applied to each of the start phases. For some interventions, the user indicates absolute changes in the respective durations of each of the start phases, e.g., to lengthen each phase by a certain number of seconds during a given period, e.g., each minute. At a routine duration set step 124, user 30 sets the total duration of the routine. The method proceeds to step 116, at which the metronome saves the routine.

Alternatively, exercise definer 34 provides the user with other methods for defining an exercise routine. For example, the user may select the start biorhythmic pattern using one of the techniques described hereinabove. The user then selects, e.g., from a menu, an indicator of desired improvement to be achieved at the end biorhythmic pattern. For example, the user may select (a) a desired ratio of start to end breathing rate, (b) a desired end ratio of inspiration to expiration (I:E ratio), and/or (c) a desired improvement in I:E ratio. Additional techniques for allowing a user to select a desired and/or appropriate end biorhythmic pattern will be evident to those skilled in the art, having read the present patent application.

In an embodiment of the present invention, UI 32 of metronome 20 presents the user with a menu (typically scrollable) of available exercises, including key parameters of each exercise. The available exercises are defined by the user, as described hereinabove with reference to FIG. 6, pre-programmed, or otherwise loaded into the device, e.g., over a communications network. The following table shows a portion of an exemplary menu of available exercises:

| | Pattern | | Duration | |
|---|---|---|---|---|
| # | Start (seconds) | End (seconds) | Modification (minutes) | Total (minutes) |
| 01 | 2,3 | 8,12 | 5 | 5 |
| 02 | 4,4 | 6,15 | 10 | 15 |
| 03 | 1,3,1 | 2,9,3 | 10 | 25 |
| 04 | 1,3,1 | 2,2,9,3 | 10 | 35 |

In this menu, the number of values provided for start and end patterns corresponds to the number of phases of the exercise, and the "Modification" column includes the length of the modification period, as described hereinabove with reference to step 112 of FIG. 6.

In an embodiment of the present invention, when user 30 selects an exercise routine, driver 36 creates an exercise pattern file based on the selected exercise routine. Alternatively, driver 36 retrieves an exercise pattern file that was previously created and stored for the selected exercise routine. To create the exercise pattern file, driver 36 uses one or more linear or non-linear algorithms. The exercise pattern file typically comprises a record for each biorhythmic pattern in a sequence of biorhythmic patterns that vary during the exercise period. The first and last records hold information regarding the start and end biorhythmic patterns, respectively, and the remaining records hold information regarding respective intermediary biorhythmic patterns. Each record comprises a phase value for each phase of the biorhythmic patterns, the phase value indicative of the duration of the phase. When the number of phases of the start and end biorhythmic patterns differ, each record comprises a number of phase values equal to the greater number of phases (typically, phases not defined for a given record are represented by zeros).

In an embodiment of the present invention, driver 36 uses the following algorithm for calculating the phase values of each record of an exercise pattern file based on an "end" type routine, as described hereinabove with reference to FIG. 6. Each record comprises N phase values 1 . . . N, where N equals the number of phases of the start or end biorhythmic pattern having the greater number of phases. The total duration of each biorhythmic pattern j, $T_j$, equals the summation of the durations of the phases of the pattern j, $T_j[1]$ ... $T_j[N]$, as follows:

$$T_j = \sum_{i=1}^{N} T_j[i]$$

The following equation gives the number of records n to be played in the exercise pattern file:

$$n=\text{INT}[(\text{duration})/((T_{start}+T_{end})/2)]$$

where INT is an integer truncation function, duration is the duration of the modification period, as described hereinabove with reference to FIG. 6, and $T_{start}$ and $T_{end}$ are the total durations of the start and end biorhythmic patterns, respectively.

The duration of any given phase k of a biorhythmic pattern j is given by the following equation:

$$T_j[k]=T_{start}[k]+j*\Delta T[k]$$

where $$\Delta T[k]=(T_{end}[k]-T_{start}[k])/n$$

For example, a start biorhythmic pattern and an end biorhythmic pattern may each have two phases. The durations of the phases of the start biorhythmic pattern may be 1 second and 2 seconds, respectively, and the durations of the phases of the end biorhythmic pattern may be 2 seconds and 6 seconds, respectively. The duration of the modification period may be 555 seconds. Therefore:

$$T_{start}=1+2 \text{ seconds}=3 \text{ seconds}$$

$$T_{end}=2+6 \text{ seconds}=8 \text{ seconds}$$

$$n=\text{INT}(555/((3+8)2))=\text{INT}(100.9)=100$$

$$\Delta T[1]=(2-1)/100=0.01 \text{ seconds}$$

$$\Delta T[2]=(6-2)/100=0.04 \text{ seconds}$$

The series of durations of the first phase is thus 1.00, 1.01, 1.02, ..., 1.99, 2.00 (101 terms), and the series of durations of the second phase is 2.00, 2.04, 2.08, ..., 5.96, 6.00 (101 terms). The actual duration of the modification period is 100*(3+8)/2=550 seconds, which is slightly shorter than the programmed 555 seconds. When the output signal comprises music, truncating the number of records to an integral value prevents prematurely ending the music in the middle of a pattern, which may sound unpleasant.

Typically, for each phase k that is included in the start biorhythmic pattern, but not in the end biorhythmic pattern, driver 36 sets $T_{end}[k]=0$. Likewise, for each phase k that is included in the end biorhythmic pattern, but not in the start biorhythmic pattern, driver 36 sets $T_{start}[k]=0$.

Alternatively, driver 36 determines the various durations by accessing an algorithm that uses a geometric series, or another series, using techniques which will be evident to those skilled in the art, having read the present patent application. Further alternatively, driver 36 uses an algorithm that varies the rate of the biorhythmic patterns, i.e., the reciprocal of duration.

In an embodiment of the present invention, driver 36 uses the following algorithm for calculating the phase values of each record of an exercise pattern file based on a "trend" type routine, as described hereinabove with reference to FIG. 6. During the duration of the routine, driver 36 calculates rate (i.e., the reciprocal of duration) of each phase k of each biorhythmic pattern j using the following equation:

$$1/T_j[k]=(1-e[k])*(1/T_{j-1}[k])$$

where e[k] is the selected change per biorhythmic pattern of phase k, and $1/T_j$ is the rate of biorhythmic pattern j.

Figure 7:
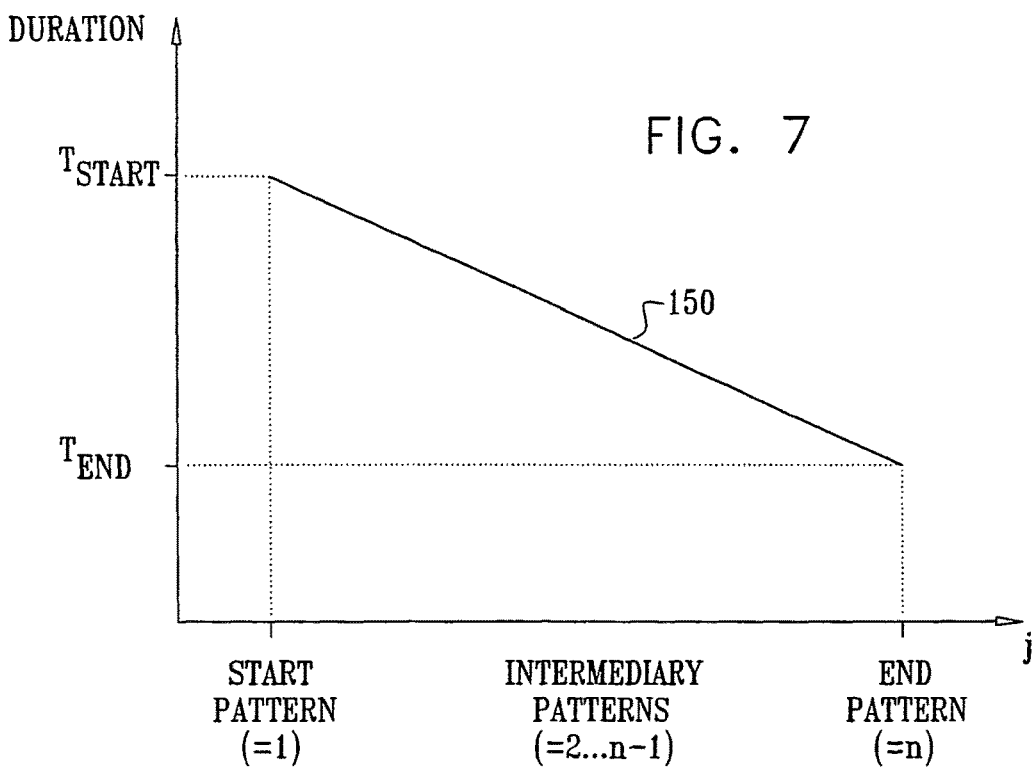
FIG. 7 is a graph showing exemplary dynamic changes in durations of a phase of a biorhythmic pattern, in accordance with an embodiment of the present invention.

Reference is now made to FIG. 7, which is a graph showing exemplary dynamic changes in durations of a phase of a biorhythmic pattern, in accordance with an embodiment of the present invention. A line 150 shows an exemplary change in duration of a single phase of a series of biorhythmic patterns, beginning with a start biorhythmic pattern, transitioning through intermediary biorhythmic patterns, and ending with an end biorhythmic pattern.

Figure 8:
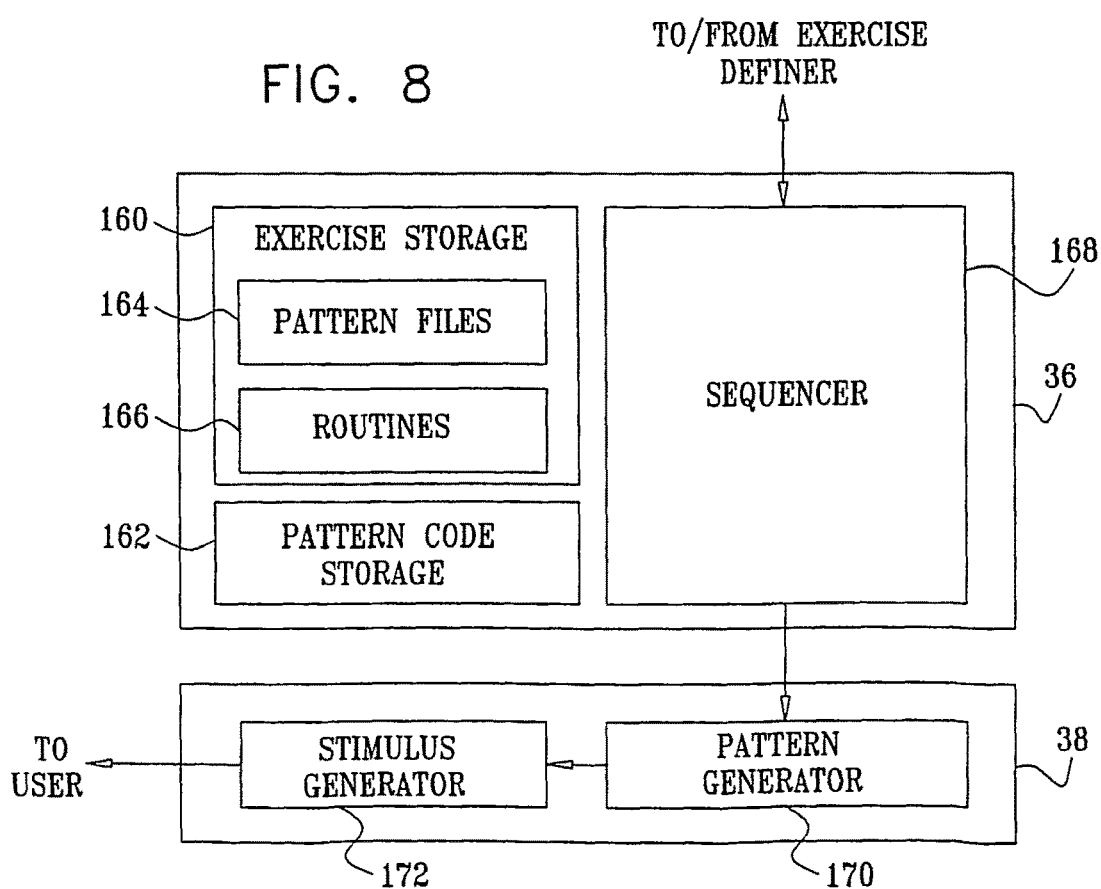
FIG. 8 is a schematic block diagram showing components of the metronome of FIG. 1, in accordance with an embodiment of the present invention.

Reference is now made to FIG. 8, which is a schematic block diagram showing components of driver 36 and biorhythmic activity modifier 38, in accordance with an embodiment of the present invention. Driver 36 comprises an exercise memory 160 and a pattern code memory 162. Exercise memory 160 comprises (a) an exercise pattern file memory 164, which stores exercise pattern files created as described hereinabove with reference to FIG. 7, and (b) an exercise routine memory 166, which stores exercise routines created as described hereinabove with reference to FIG. 6, or otherwise pre-programmed or loaded into metronome 20.

Driver 36 further comprises a sequencer 168, which, during execution of an exercise routine by driver 36, generates temporal code and passes the temporal code to biorhythmic activity modifier 38. Sequencer 168 retrieves an exercise pattern file from pattern file memory 164, and a pattern code from pattern code memory 162, and combines information from the exercise pattern file with the pattern code, in order to generate the temporal code, as described hereinbelow. Sequencer 168 typically performs such retrieval either upon initiation of an exercise routine, or throughout the exercise routine as the sequencer generates the temporal code.

For applications in which the output signal comprises music, the pattern code contains elements indicating musical information, such as notes and/or type of synthesized instrument, for each phase of each biorhythmic pattern of the selected exercise pattern file. For example, a two-phase exercise pattern may have two synthesized instrument sounds A and B corresponding to the first phase and second phase, respectively. The pattern code has the structure $A_1$, $B_1$, $A_2$, $B_2$, $A_3$, $B_3$, ..., where $A_i$ and $B_i$ each represent a series of musical notes associated with one or more synthesized instrument sounds. The instrument sounds associated with $A_i$ and $B_i$ may be the same or different from each other.

Continuing the two-phase example, $A_i$ may represent a series of notes to be generated using a synthesized flute sound, while $B_i$ may represent a series of notes to be generated using synthesized trumpet and violin sounds. The exercise pattern may include a biorhythmic pattern comprising 2 seconds of a phase 1 followed by 4 seconds of a phase 2, and $A_1$ may represent a series of two flute notes, while $B_1$ represents a series of two trumpet notes followed by one violin note. Sequencer 168 combines the information from phase 1 and phase 2 of the biorhythmic pattern with $A_1$ and $A_2$ of the pattern code, respectively, to produce temporal code. The temporal code would include: an ON signal for series $A_1$, followed, 2 seconds later, by an OFF signal for series $A_1$ and an ON signal for series $B_1$, followed, 4 seconds later, by an OFF signal for series $B_1$, etc.

Reference is again made to FIG. 8. Biorhythmic activity modifier 38 comprises a pattern generator 170 and a stimulus generator 172. Pattern generator 170 converts the temporal code into signals for driving stimulus generator 172. For some applications, pattern generator 170 comprises a sound synthesizer, and stimulus generator 172 comprises one or more speakers 40 (FIGS. 2, 3, and 9), in which case pattern generator 170 converts the musical temporal code into electrical current for driving the speakers to create sound.

Alternatively, stimulus generator 172 comprises:
- a visual stimulator, such as a display, which may include a digital display screen and/or one or more cue lights. Display screen 52 (FIG. 2) or monitor 64 (FIG. 3) may be configured to function as the visual display;
- a pressure applicator, such as a pressure cuff 174 mounted on an arm 176 of user 30 (FIG. 2), which, for some applications, is configured to massage the arm. The pattern code includes ON and OFF signals, which biorhythmic activity modifier 38 converts to electrical signals to drive a pump that inflates and deflates cuff 174 (pump not shown);
- a mechanical stimulator; and/or
- an electrical stimulator.

In an embodiment of the present invention, the user stimulus is in the form of a game, and the parameters of the game are altered so that playing the game induces the user to modify a parameter of the biorhythmic activity.

Reference is now made to FIG. 9, which is a schematic illustration of an implementation of metronome 20 over a telephone network 200, in accordance with an embodiment of the present invention. In this embodiment, stimulus generator 172 typically comprises a speaker 202 of a conventional wired or wireless telephone 204, and UI 32 comprises a keypad 206 of the telephone. The remaining components of metronome 20 are implemented remotely from user 30, such as at a telephone company station or at another service provider. Telephone 204 is connected to such remote metronome functionality 210 wirelessly or over telephone wires, typically through at least one telephony switch 212. Alternatively, UI 32 comprises a microphone 208 of telephone 204, and functionality to interpret voice commands of user 30, and/or for sensing respiration of user 30 for programming metronome 20, as described hereinabove with reference to FIG. 6.

In an embodiment of the present invention, metronome 20 is implemented over telephone network 200 using dual tone multi-frequency (DTMF) signals, which are generated by the user using keypad 206 and decoded by remote metronome functionality 210. The following table sets forth an exemplary implementation of such a system. It is to be understood that the details given in the table are for illustrative purposes only, and numerous alternative approaches will be apparent to those skilled in the art, having read the present application.

| Step # | User action | System action |
|---|---|---|
| 1 | Calls the service number. | Human voice: "Welcome to the 'Breathe With Us' service. Please enter your personal code." |
| 2 | Keys in personal code. | Human voice: "To select one of your previous exercises, press 1. "To select a new exercise, press 2. "To hear a demo, press 3. "To select the sound, press 4 at any time. "For help, press 111 at any time. "To proceed with a step press the pound key at any time. "To return to a previous step press the star key at any time. "To exit press 0 at any time." |
| 3 | Presses 1 in response to step 2. | Human voice: "Key in an exercise number or press 11 to hear a list (with scrolling using the pound and star keys)." |
| 4 | Enters exercise number in response to step 3. | The system goes to step 19. |
| 5 | Presses 11 in response to step 3. | Human voice: "To select an exercise from the following list, press 1. "To delete an exercise, press 999. "Exercise #1 includes slowing down your breathing from 15 times per minute with inspiration to expiration counts 1:2 to breathing at 6 times per minute with counts 1:4. "Press 1 to select." [Short pause.] "Exercise #2 . . ." |
| 6 | Selects an exercise by pressing a corresponding number, in response to step 5. | The system goes to step 19. |
| 7 | Presses 2 in response to step 2. | Human voice: "For a breathing pattern including inspiration and expiration press 21. "For a breathing pattern including inspiration, breath holding and expiration press 22. "For a breathing pattern including inspiration, breath holding, expiration and 'rest' press 23." |
| 8 | Presses 21 in response to step 7. | Human voice: "Press the pound key when you begin inspiration, then press the pound key again when you begin expiration, and, finally, press the pound key again when you begin a new inspiration." |
| 9 | Presses pound key at start/end of each phase, in response to step 8. | A voice counts 1, 2, 3, 4 . . . at one-second intervals and starts recounting at the beginning of each phase. Upon finishing, human voice: "You have selected_counts for inspiration and_counts for expiration. Your selected pattern will be played until you press the pound key." The system plays the pattern using default orchestration. |
| 10 | | Human voice: "To select your target breathing pattern press 200. "To select a trend of change press 210." |
| 11 | Presses 200 in response to step 10. | The system uses the procedure of steps 8-9, and then goes to step 17. |
| 12 | Presses 210 in response to step 10. | Human voice: "Enter the percentage by which you would like the duration of each inspiration to increase from one breath to the next. Typical values are 5% to 15%." |
| 13 | Enters percentage. | Human voice: "Enter the percentage by which you would like the duration of each expiration to increase from one breath to the next. Typical values are 5% to 15%." |
| 14 | Enters percentage. | Human voice: "Enter for how many minutes you would like to generate changes in your breathing pattern." |
| 15 | Enters duration. | System calculates the end pattern, converts it to the closest "counts structure," describes its structure as in step 9, and, using a default orchestration, plays the end pattern until the pound key is pressed. |
| 16 | Presses pound key, in | Human voice: "Enter additional minutes |

| Step # | User action | System action |
|---|---|---|
| | response to step 15. | to continue after end pattern. If none, press the pound key." |
| 17 | Enters additional minutes or presses the pound key. | Human voice: "To save the exercise press 50. "To start the exercise press the pound key. "To exit press 0." |
| 18 | Presses 50 in response to step 17. | Human voice: "The exercise has been saved under number [xxx] at [date]." The system goes to step 17. |
| 19 | Presses the pound key in response to step 17. | Human voice: "Enjoy the exercise. If you want to know how much time is left, press 1 at any time." The system calculates the exercise pattern file or locates in memory the appropriate sequence. The system activates the sound system to play the musical stimulus. When the time-limit has been exceeded, human voice: "Thank you for breathing with us." The system concludes the method. |
| 20 | Presses 1 in response to step 19. | A voiceover provides the remaining time. |
| 21 | Presses 4 at any time. | Human voice: "Select your favorite orchestra from the list by pressing the pound key to scroll through available options, and pressing the pound key to return. To exit and keep this sound, press 1." The system goes to step 2 |
| 22 | Presses 1 in response to step 21. | Voice presenting the orchestration title e.g., "Bamboo dance." The system plays the initial pattern using the selected orchestration. The system goes to step 2. |
| 23 | Presses 3 in response to step 2. | Human voice: "Here is a demo that demonstrates to you the power of the 'Breathe With Us' service." The system plays a sample with voice-over explaining its main features. The system goes to step 2. |

Reference is again made to FIGS. 2, 3, and 9. In an embodiment of the present invention, metronome 20 comprises (a) a library of exercise output signals, comprising music, generated by biorhythmic activity modifier 38, using a plurality of respective pre-exercise defined exercise routines, and (b) means for playing music stored in the library. For some applications, metronome 20 comprises a conventional music player, such as a compact disc (CD) player or a tape player (a portable configuration is shown in FIG. 2), and the music is stored on a non-volatile medium, such as a CD or audio tape. Alternatively, metronome 20 comprises conventional audio software running on computer 60 (FIG. 3) or metronome functionality 210 (FIG. 9), in which case the music is either stored on a non-volatile medium, such as a CD or DVD, or is stored in memory, such as after being downloaded over the Internet. For some applications, the music is represented using the Musical Instrument Digital Interface (MIDI) protocol, and software on computer 60 or metronome functionality 210 interprets the MIDI information to synthesize the music. Each exercise in the library is typically identified by the parameters, or a subset thereof, that define the exercise routine upon which the exercise is based (such parameters are described hereinabove with reference to FIG. 6).

In this embodiment, user 30 uses UI 32 to select an exercise, i.e., a piece of music, from the library. For some applications, UI 32 is configured as described hereinabove with reference to the table showing the portion of the exemplary menu of available exercises. Alternatively, UI 32 comprises the conventional UI of a conventional music player or conventional audio software, as appropriate. In this configuration, the name of each piece of music typically includes one or more key parameters of the exercise. For example, a piece of music based on a two-phase exercise routine that begins at 20 breaths per minute (bpm) with an inspiration to expiration (I:E) ratio of 1:1, and ends at 6 bpm with an I:E ratio of 1:3, may have a name such as "Song 5/from 20 bpm ratio 1:1 to 6 bpm ratio 1:3". Alternatively, the user is instructed to count his or her number of breaths over a set period of time, e.g., one minute, and to select the piece of music having a number corresponding to the number of breaths.

Typically, the exercises included in the library are selected so as to offer user 30 a sufficiently wide variety of options, while at the same time generally limiting the total number of selections. Such limiting of selections may reduce the amount of storage needed for the library, and/or increase the efficiency and/or ease with which the user selects the desired exercise.

In an embodiment of the present invention, the exercises included in the library are selected so as to provide several options for a few significant end parameters, such as number of end phases, end bpm, and end I:E ratio. Fewer options for start parameters, or only a single option, are typically offered. As long as the chosen start parameters are within normal breathing patterns for most users, such a lack of options does not generally inconvenience the user. For some applications, the start bpm may be faster than the natural bpm of most users, e.g., 20 bpm, and the user may be instructed to fast-forward to the point in the selected piece of music at which the bpm has slowed to the user's current bpm. The total number of permutations typically results in an amount of stored music that can be stored, for example, on only one, two, or three conventional CDs.

For example, the library may include exercises based on the following parameters:
start parameters: (a) 20 bpm, and (b) an I:E ratio of 1:1; and
end parameters: (a) 10, 6, or 4 bpm, and (b) two-phase I:E ratios of 1:2, 1:3, or 1:4, or three-phase I:E ratios of 1:1:1, 1:1:3, or 2:1:2.

Alternatively or additionally, for some interventions, the library includes exercises that modify the user's I:E ratio without changing the rate of breathing. For example, the exercise may have a constant bpm of 10, and the I:E ratio may start at 1:1 and end at 1:4 after 10 minutes. Such exercises may be useful for users suffering from some breathing disorders.

In an embodiment of the present invention, metronome 20 stores a limited number of exercises, either as pieces of music or as exercise pattern files. Metronome 20 provides user 30 with the option of defining a desired exercise routine, such as described hereinabove with reference to FIG. 6. However, rather than generate music or an exercise pattern file, as the case may be, on the fly, metronome 20 selects the pre-stored piece of music or exercise pattern file, as the case may be, most similar to the desired routine. Optionally, the metronome is configured to begin playing the pre-stored piece of music, or interpreting the pre-stored exercise pattern file, as the case may be, at a point later than the beginning thereof, in order to better match the user's desired exercise routine. For example, if the user selects a routine having start parameters that includes inspiration for 1.02 seconds and expiration for 2.1 seconds, and the metronome has stored the exemplary 550-second two-phase exercise pattern file described hereinabove, the metronome may begin the exercise using the third pattern in the stored time series. For selected parameters that do not precisely match one of the stored patterns, the metronome typically selects the stored pattern that most closely matches the selected parameters.

Metronome 20 is suitable for use in a number of applications, including those set forth in the following table:

| Application | Configuration of metronome 20 | Operation |
| --- | --- | --- |
| Treatment by starting with normal breathing and achieving slow breathing with extended expiration. | As described herein | As described herein |
| Treating patients with Chronic Obstructive Pulmonary Disease (COPD) by retaining breathing with a resistive load during inspiration, and attempting to achieve target frequency with a specific inspiration/expiration time ratio. | Comprises (a) a resistive load that resists airflow during inspiration (or expiration), and/or (b) additional memory for the date and time of device use, which enables a healthcare professional to evaluate compliance with use instructions. | There is a specific end pattern to achieve, e.g. 15 breaths per minute with inspiration time 2.5 sec and expiration 1.5 sec, or per the recommendation of a healthcare professional or exercise instructor. |
| Treatment by physical exercise including both body movements and breathing. | Comprises a tactile stimulus for guiding breathing and audio stimulus for guiding other body movements, typically implemented using the embodiment shown in FIG. 2. | For example, raising hands for four beats (phases 1 to 4) and lowering hands for two beats (phases 4 to 6). At the same time "breath in" vibratory stimulus is applied during phases 1 to 4. |
| Treatment for exercising malfunctioning muscle groups. | Comprises electrodes adapted to stimulate muscles. | |
| Getting do-it-at-home instructions by an instructor, such as a yoga master, who defines the exercise during a conventional class. | | |
| Stand-alone system that modifies movement in sport training. | For example, comprises a watch worn on the hand of an exerciser in aerobic or other types of exercises with multi-phase patterns. | |
| A stand-alone message system for the digits using pressure stimulus. | Comprises a pressure applicator. | |
| A PC-based system for relaxation at the worksite. | Software only, audio-visual stimulus, all required hardware platform already exists. | |

In an embodiment of the present invention, metronome 20 is adapted to perform the intervention by generating a user stimulus to which user 30 reacts involuntarily. Typically, such an involuntary user stimulus is applied slightly out of phase with the biorhythmic activity it is desired to modify, for example, respiration. This approach may be used, for example, when the user is a subject whose autonomic control of breathing is impaired, such as an unconscious subject (e.g., when the subject is in a coma or under anesthesia). Additionally, this approach may be used when the user is sleeping, such as when the user suffers from sleep apnea caused by the user's inadequate control over breathing. For example, by auditory or other stimulation, the intervention may stimulate respiratory muscles of an unconscious user who is spontaneously breathing. Further additionally, this approach may be used when the user is mechanically ventilated.

Even when an intervention is applied to a conscious user, for some applications, the user semi-consciously or unconsciously modifies an aspect of voluntary action. For example, many people unconsciously and effortlessly entrain their breathing, walking, or running to an outside rhythmic stimulus, such as strongly-rhythmic music or even a blinking light. Similarly, some of these embodiments of the present invention may be applied to people who are not consciously attempting to coordinate the voluntary action with the rhythm of the applied intervention. Thus, for some applications, a user of some of these embodiments may read, talk, eat, or even sleep, while an intervention such as is described herein is applied to the user. For example, an application running in the background on a user's personal computer may play a musical pattern while the user is working.

In an embodiment of the present invention, metronome 20 guides user 30 to change his or her breathing pattern in a way that typically increases tissue oxygenation. This application of the present invention is particularly useful in the treatment of congestive heart failure (CHF), which often causes afflicted patients to demonstrate Cheyne-Stokes respiration. This breathing pattern leads to a drop in average tissue oxygenation, because excessively-slow breathing does not supply sufficient levels of oxygen to the body, and hyperventilation places a severe load on the patient's already weak heart and does not optimally oxygenate the body. Typically, musical patterns include musical or vocal guidance to the user to inhale and to exhale according to a schedule which gradually brings his respiration into a desired, healthy pattern, so as to increase tissue oxygenation. In accordance with an embodiment of the present invention, protocols described in the above-cited articles by Mortara and Bernardi are utilized in applying the techniques described herein, so as to obtain desired increases in tissue oxygenation. The musical or vocal guidance to inhale may include, for example, a flute playing a sequence of notes which generally rises in pitch and/or volume, while the direction to exhale may include cello or guitar notes which fall in pitch and/or volume. Alternatively, the user is instructed at the beginning of the session to inhale whenever he hears a flute or a tone having a specified high pitch, and to exhale whenever he hears the cello, guitar or a tone having a specified low pitch. Protocols for generating the music are described in the above-referenced U.S. patent application Ser. No. 09/611,304 and '049 PCT Publication, particularly with reference to FIG. 16 thereof.

Alternatively or additionally, metronome 20 is operated so as to increase the mechanical compliance of the user's blood vessels. This compliance reflects the ability of blood vessels to expand in response to passage therethrough of blood ejected from the heart. Sufficient levels of arterial compliance are known to be important in buffering the pulsatile pattern of the blood pushed at high pressure from the heart, thereby smoothing the flow of blood into the microvasculature. Reduced arterial compliance, by contrast, is associated with improper function of baroreceptors which are used by the body in the feedback systems which control blood pressure. Arterial compliance is known to decrease with increasing age, as well as in many cardiovascular diseases, such as hypertension, congestive heart failure, and atherosclerosis. Moreover, arterial compliance decreases in response to an acute increase in blood pressure, and in response to increased sympathetic nervous activity, e.g., when a person is experiencing mental stress. Alternatively or additionally, metronome 20 is operated so as to reduce peripheral impedance of small blood vessels of the user, to increase heart rate variability of the user, and/or to increase baroreflex sensitivity of the user.

Typically, metronome 20 increases arterial compliance in a manner generally analogous to that described hereinabove with respect to increasing blood oxygenation. The inventor has found that many cardiovascular indicators are optimized by causing the respiration rate or another voluntary or involuntary physiological parameter of the user to cycle at approximately 6 repetitions per minute.

In cases where a patient has COPD, it is known in the art to instruct the patient to increase his respiratory endurance by breathing 15 breaths per minute through an inspiratory load, while spending 60% of each respiratory cycle inhaling, and 40% of the cycle exhaling. Because of the high levels of mental concentration and physical effort that such an exercise requires, and because of the relatively boring nature of the task, most patients have difficulty following such a regimen without the use of metronome 20, and even dedicated patients tend to stop performing the exercise except under the direct supervision of a healthcare worker.

In an embodiment of the present invention, metronome 20 comprises a sensor adapted to detect a physiological event of subject 30. When the event is detected, metronome 20 typically determines the start biorhythmic pattern at least in part responsively to a signal generated by the sensor. For example, the event may be an episode of abnormal breathing, such as sleep apnea, in which case the sensor may detect cessation of breathing, a sudden change in heart rate, or any other indication of apnea. Upon detection of the abnormal breathing, metronome 20 initiates multi-phase audio, electrical, or other stimulation described herein in an attempt to restore normal breathing. For some applications, prior to initiating the stimulation, metronome 20 substantially continuously monitors one or more physiological variables, such as pulse or respiration, and analyzes the variables to determine the durations of the phases of the start biorhythmic pattern. Typically, a library of stimulations is provided, from which metronome 20 selects the most effective corresponding start biorhythmic pattern and trend or end parameters, using stored patterns or algorithms. Alternatively, the metronome sets the start biorhythmic pattern responsive to the abnormal breathing pattern detected during apnea. Generally, applying stimulation based on the start biorhythmic pattern mimics the voluntary control of breathing sometimes necessary to restore normal breathing to a subject experiencing an episode of sleep apnea.

In some embodiments of the present invention, by contrast, the mental effort is substantially eliminated, because user 30 need only listen to the music and breathe in accordance with its rhythm and pattern. In addition, this embodiment provides significantly more functionality than would, for example, an "inhalation indicator light," which simply has a 60% duty cycle and turns on 15 times per minute. Metronome 20, by contrast, typically gradually changes the user's breathing pattern from its initial measured or estimated state (e.g., 8 breaths per minute, 30% inhale and 70% exhale) to the desired final state. Typically, this change is caused by guiding the user's respiration through a two-dimensional parameter space defined by {[Breathing Rate], [Inspiration:Expiration Ratio]}. Typically, metronome 20 guides the user's respiration from a point in the space representing the initial state, along a path through the space (e.g., the shortest path through the space), to a point in the space representing the desired final state.

It is known that the respiratory system of some patients is slow to recover following surgery, and that other patients take days or weeks to successfully wean themselves from a mechanical ventilator. Therefore, some applications of the present invention are directed towards using the apparatus and methods described herein, mutatis mutandis, to gradually retrain ventilator-dependent or post-surgery patients in proper breathing techniques. Many mechanical ventilators for use with alert patients are triggered to support the patients' breathing efforts, rather than to dictate the timing and depth of every breath. In ventilator-weaning embodiments of the present invention in which the user exercises voluntary control over his/her own breathing, patient-triggered ventilators are typically utilized in combination with metronome 20.

Techniques described herein may be practiced in conjunction with techniques described in the above-referenced U.S. patent application Ser. No. 09/611,304 and '049 PCT Publication.

It will be understood that whereas embodiments of the present invention have sometimes been described with respect to a user having a pathology, it is within the scope of the present invention for the user to be generally healthy, and to choose to use aspects of the present invention in order to obtain psychological stress-relief and/or relaxation, or for purposes of muscle re-education, athletic training, or entertainment.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An exercise device for modifying a multi-phase biorhythmic activity of a subject, the exercise device comprising:
   a memory storing:
      a set of computer instructions,
      an initial multi-phase biorhythmic activity pattern, and
      an a-priori determined desired multi-phase biorhythmic activity pattern,
         wherein at least one ratio between a duration of two phases in the initial multi-phase biorhythmic activity pattern is different from a corresponding ratio in the a-priori determined desired multi-phase biorhythmic activity pattern, and
         wherein the initial multi-phase biorhythmic activity pattern characterizes the actual multi-phase biorhythmic activity pattern of the subject at the time of use; and
   a stimulus generating unit comprising a processor, the stimulus generating unit configured to:
      generate, responsive to the stored set of computer instructions, a time-varying stimulus that has a multi-phase pattern comprising a plurality of transitional forms, generated according to predetermined rules, intermediate of the initial multi-phase biorhythmic activity pattern and the desired multi-phase biorhythmic activity pattern; wherein each subsequent transitional form has a multi-phase biorhythmic activity pattern more similar to the desired multi-phase biorhythmic activity pattern than a multi-phase biorhythmic activity pattern of a previous transitional form;

provide the defined time-varying stimulus to the subject including the plurality of transitional forms; and guide the subject to modify the multi-phase biorhythmic activity pattern, such that the duration ratio of the at least two phases of the multi-phase biorhythmic activity pattern transitions into the duration ratio of the desired multi-phase biorhythmic activity pattern during the providing of the defined time varying stimulus, and such that the stimulus generating unit provides instructions to the subject to request that the subject synchronize the multi-phase biorhythmic activity with the time-varying stimulus;

wherein the time-varying stimulus and rules for generating said transitional forms are defined prior to the step of providing the defined time-varying stimulus to the subject and are independent of ongoing measurement of the multi-phase biorhythmic activity, wherein at least one phase of the multi-phase biorhythmic activity pattern of the time-varying stimulus corresponds to a respective phase of the multi-phase biorhythmic activity of the subject, and wherein the duration of both the initial multi-phase biorhythmic activity pattern and the a-priori determined desired multi-phase biorhythmic activity pattern are predetermined prior to the stimulus generation, wherein the duration of each transitional form varies linearly or geometrically over time.

2. The exercise device of claim 1, wherein the time-varying stimulus comprises music, wherein the stimulus unit comprises a music synthesizer, configured to generate the music.

3. The exercise device of claim 1, further comprising a sensor, configured to sense a physiological event and to generate an event signal responsive thereto, and wherein the stimulus unit is configured to commence defining the time-varying stimulus responsive to the event signal.

4. The exercise device of claim 1, wherein the memory is configured to have stored therein a plurality of exercise routines having respective initial forms and respective indications of desired forms, wherein the stimulus unit comprises a user interface, configured to enable the subject to select one of the exercise routines, and wherein the stimulus unit is configured to define the time-varying stimulus responsive to the selection.

5. The exercise device of claim 4, wherein the user interface comprises a user interface of an audio-playback device or a general-purpose computer.

6. The exercise device of claim 1, wherein the biorhythmic activity of the subject comprises respiration.

7. The exercise device of claim 6, wherein two or more phases in the desired form include at least one respiration phase not generally included in the multi-phase biorhythmic activity prior to defining the time-varying stimulus, and wherein the memory is configured to have stored therein an indication of the at least one respiration phase.

8. The exercise device of claim 6, wherein the at least two phases include at least one respiration phase selected from the list consisting of: breath holding and post-expiratory pausing, and wherein the memory is configured to have stored therein an indication of the selected respiration phase.

9. The exercise device of claim 6, wherein the at least two phases in the initial and the desired forms include inspiration and expiration, wherein the ratio of duration of the inspiration to the duration of the expiration (I:E ratio) in the desired form is less than the I:E ratio in the initial form.

10. The exercise device of claim 1, further comprising a user interface, configured to receive input from the subject, wherein the apparatus is configured to store the initial form and the indication of the desired form in the memory, responsive to the input.

11. The exercise device of claim 10, wherein the user interface is configured to receive the duration ratio of the at least two phases in the initial form.

12. The exercise device of claim 10, wherein the user interface is configured to measure a lapse between a start indication and an end indication of at least one of the phases in the initial form.

13. The exercise device of claim 12, wherein the start and end indications include respective audible indications of respiration of the subject, and wherein the user interface is configured to sense the audible start and end indications.

14. A method for modifying a biorhythmic activity of a subject, the method comprising the steps of:

storing an initial multi-phase biorhythmic activity pattern and an a-priori determined desired multi-phase biorhythmic activity pattern, wherein at least one ratio between a duration of two phases in the initial multi-phase biorhythmic activity pattern is different from a corresponding ratio in the desired multi-phase biorhythmic activity pattern, and wherein the initial multi-phase biorhythmic activity pattern characterizes the actual multi-phase biorhythmic activity pattern of the subject at the time of use;

generating a time-varying stimulus that has a multi-phase pattern that is characterized by a plurality of transitional forms generated according to predetermined rules, intermediate of the initial multi-phase biorhythmic activity pattern and the desired multi-phase biorhythmic activity pattern, wherein each subsequent transitional form has a multi-phase biorhythmic activity pattern more similar to the desired multi-phase biorhythmic activity pattern than a multi-phase biorhythmic activity pattern of a previous transitional form;

providing the defined time-varying stimulus to the subject including the plurality of transitional forms; and guiding the subject to modify the multiphase biorhythmic activity, such that the duration ratio of the at least two phases of the multi-phase biorhythmic activity pattern transitions into the duration ratio of the desired multi-phase biorhythmic activity pattern during the providing of the defined time varying stimulus, wherein the guiding of the subject comprises requesting the subject to synchronize the biorhythmic activity with the guiding stimulus;

wherein the time varying stimulus and rules for generating said transitional forms are defined prior to the providing thereof and independently of ongoing measurement of the multi-phase biorhythmic activity pattern, wherein at least one phase of the multi-phase biorhythmic activity pattern corresponds to a respective phase of a multi-phase biorhythmic activity of the subject, and wherein the duration of both the initial multi-phase biorhythmic activity pattern and the a-priori determined desired multi-phase biorhythmic activity pattern are predetermined prior to the stimulus generation, wherein the duration of each transitional form varies linearly or geometrically over time.

15. The method of claim 14, wherein the time-varying stimulus includes music, and wherein defining the time-varying stimulus comprises generating the music.

16. The method of claim 14, comprising sensing, prior to defining the time-varying stimulus, a physiological event, wherein defining the time-varying stimulus comprises commencing defining the time-varying stimulus responsive to the sensing of the physiological event.

17. The method of claim 14, wherein storing comprises storing a plurality of exercise routines having respective initial forms and respective indications of desired forms, and wherein defining the time-varying stimulus comprises selecting one of the exercise routines.

18. The method of claim 17, wherein selecting the one of the exercise routines comprises using a user interface of an audio-playback device or a general-purpose computer to select the one of the exercise routines.

19. The method of claim 14, wherein the multi-phase biorhythmic activity includes respiration of the subject, and wherein defining the time-varying stimulus comprises configuring the time-varying stimulus to guide the subject to modify the respiration.

20. The method of claim 14, wherein storing the initial form and the indication of the desired form comprises receiving an input from the subject.

21. The method of claim 20, wherein receiving the input comprises measuring a lapse between a start indication and an end indication of at least one of the phases in the indication of the initial form.

22. The method according to claim 21, wherein the start and end indications include respective audible indications of respiration of the subject, and wherein measuring the lapse comprises sensing the audible start and end indications.

23. A computer software product used to modify a muscle activity of a subject, the computer software product comprising:
 a non-transitory computer readable medium storing program instructions, the instructions comprising:
  an initial multi-phase biorhythmic activity pattern and an a-priori determined desired multi-phase biorhythmic activity pattern, wherein at least one ratio between a duration of two phases in the initial pattern is different from a corresponding ratio in the desired pattern,
  wherein the initial multi-phase biorhythmic activity pattern characterizes the actual multi-phase biorhythmic activity pattern of the subject at the time of use,
 wherein the instructions, when read by a computer, cause the computer to:
  generate a time-varying stimulus that has a multi-phase pattern comprising a plurality of transitional forms generated according to predetermined rules, intermediate the initial form of the multi-phase biorhythmic activity pattern and the desired form of the multi-phase biorhythmic activity pattern, wherein each subsequent transitional form has a multi-phase biorhythmic activity pattern more similar to the desired multi-phase biorhythmic activity pattern than a multi-phase biorhythmic activity pattern of a previous transitional form;
  provide the defined time-varying stimulus to the subject,
  guide the subject to modify the multi-phase biorhythmic activity, such that the duration ratio of at least two phases of the multi-phase biorhythmic activity transitions into the duration ratio of the desired multi-phase biorhythmic activity pattern during the providing of the defined time varying stimulus,
  wherein the guiding of the subject comprises providing instructions to request the subject to synchronize the biorhythmic activity with the guiding stimulus;
 wherein at least one phase of the multi-phase biorhythmic activity pattern of the time-varying stimulus corresponds to a respective phase of the multi-phase biorhythmic activity,
 wherein the program instructions, when read by the computer, cause the computer to define the time-varying stimulus and rules for generating said transitional forms prior to the providing thereof and independently of ongoing measurement of the multi-phase biorhythmic activity, and
 wherein the duration of both the initial multi-phase biorhythmic activity pattern and the a-priori determined desired multi-phase biorhythmic activity pattern are predetermined prior to the stimulus generation,
 wherein the duration of each transitional form varies linearly or geometrically over time.

24. The product of claim 23, wherein the time-varying stimulus comprises music, and wherein the instructions cause the computer to generate the music.

25. The product of claim 23,
 wherein the non-transitory computer-readable medium is configured to have stored therein a plurality of exercise routines having respective initial forms and respective indications of desired forms,
 wherein the computer has a user interface, and
 wherein the instructions cause the computer to (a) receive, via the user interface, a selection by the subject of one of the exercise routines, and (b) define the time-varying stimulus responsive to the selection.

26. The product according to claim 23, wherein the multi-phase biorhythmic activity includes respiration of the subject, and wherein the instructions cause the computer to configure the time-varying stimulus to guide the subject to modify the respiration.

27. The apparatus of claim 1, wherein the time-varying stimulus comprises at least one stimulus selected from the list consisting of: an image, alphanumeric text, a sound, a sound pattern, a dynamic graphical pattern, and a visual cue, and wherein the stimulus unit comprises a visual stimulator, configured to define the selected time-varying stimulus.

28. The apparatus of claim 1, wherein the time-varying stimulus comprises pressure, and wherein the stimulus unit comprises a pressure applicator, configured to apply the pressure to a portion of a body of the subject.

29. The apparatus of claim 3, wherein the apparatus is configured to configure the initial form at least in part responsively to a parameter of the event signal.

30. The apparatus of claim 9, wherein the I:E ratio in the desired form is between about 1:0.5 and 1:4.

31. The apparatus of claim 10, wherein the user interface is configured to receive indications of trends over time of the durations of the two or more phases in the initial multi-phase biorhythmic activity pattern.

32. The apparatus of claim 10, wherein the user interface is configured to receive an indication of the durations of two or more phases in the desired multi-phase biorhythmic activity pattern.

33. The apparatus of claim 12, wherein the user interface is configured to receive the start and end indications from the subject at respective times, and to measure the lapse responsive thereto.

34. The method of claim 14, wherein the time-varying stimulus includes at least one stimulus selected from the list consisting of: an image, alphanumeric text, a sound, a sound pattern, a dynamic graphical pattern, and a visual cue, and wherein defining the time-varying stimulus comprises defining the selected stimulus.

35. The method of claim 14, wherein the time-varying stimulus includes pressure, and wherein defining the time-varying stimulus comprises applying the pressure to a portion of a body of the subject.

36. The method of claim 16, wherein storing the initial form comprises configuring the initial form at least in part responsively to a parameter of the physiological event.

37. The method of claim 19, wherein two or more phases in the desired form include at least one respiration phase not generally included in the multi-phase biorhythmic activity prior to defining the time-varying stimulus, and wherein storing comprises storing an indication of the at least one respiration phase.

38. The method of claim 19, wherein the at least two phases in the desired form include at least one respiration phase selected from the list consisting of: breath holding and post-expiratory pausing, and wherein storing comprises storing an indication of the selected respiration phase.

39. The method of claim 19, wherein the at least two phases in the initial and the desired forms include inspiration and expiration, and wherein storing comprises storing the initial form and the indication, wherein a ratio of a duration of the inspiration to a duration of the expiration (an I:E ratio) in the desired form is less than an I:E ratio in the initial form.

40. The method of claim 20, wherein the I:E ratio in the desired form is between about 1:0.5 and 1:4.

41. The method of claim 20, wherein receiving the input comprises receiving an indication of durations of two or more phases in the desired form.

42. The method of claim 20, wherein receiving the input comprises receiving indications of trends over time of respective durations of the at least two phases in the initial form.

43. The method of claim 20, wherein receiving the input comprises receiving an indication of durations of the at least two phases in the initial form.

44. The method of claim 21, comprising receiving the start and end indications from the subject at respective times, wherein measuring the lapse comprises measuring the lapse responsive thereto.

45. The product of claim 23, wherein the time-varying stimulus comprises at least one stimulus selected from the list consisting of: an image, alphanumeric text, a sound, a sound pattern, a dynamic graphical pattern, and a visual cue, and wherein the instructions cause the computer to define the selected time-varying stimulus.

46. The product of claim 23, wherein the time-varying stimulus comprises pressure, and wherein the instructions cause the computer to drive a pressure applicator to apply the pressure to a portion of a body of the subject.

47. The product of claim 23, wherein the instructions cause the computer to:
receive an event signal, prior to defining the time-varying stimulus, from a sensor configured to sense a physiological event and to generate the event signal responsive thereto, and
commence defining the time-varying stimulus responsive to the event signal.

48. The product according to claim 47, wherein the instructions cause the computer to configure the initial form at least in part responsive to a parameter of the event signal.

49. The product of claim 26, wherein two or more phases in the desired form include at least one respiration phase not generally included in the multi-phase biorhythmic activity prior to defining the time-varying stimulus, and wherein the instructions cause the computer to define the time-varying stimulus having an indication of the at least one respiration phase.

50. The product of claim 26, wherein the at least two phases in the desired form include at least one respiration phase selected from the list consisting of: breath holding and post-expiratory pausing, and wherein the instructions cause the computer to define the time-varying stimulus having an indication of the selected respiration phase.

51. The product of claim 26, wherein the at least two phases in the initial and the desired forms include inspiration and expiration, and wherein a ratio of a duration of the inspiration to a duration of the expiration (an I:E ratio) in the desired form is less than an I:E ratio in the initial form.

52. The product of claim 51, wherein the I:E ratio in the desired form is between about 1:0.5 and 1:4.

53. The product of claim 23, wherein the computer has a user interface, and wherein the instructions cause the computer to receive input from the subject, via the user interface, and to store the initial form and the indication of the desired form, responsive to the input.

54. The product of claim 53, wherein the instructions cause the computer to receive, via the user interface, the duration of the at least two phases in the desired form.

55. The product of claim 53, wherein the instructions cause the computer to receive, via the user interface, indications of trends over time of respective durations of the at least two phases in the initial form.

56. The product of claim 53, wherein the instructions cause the computer to receive, via the user interface, an indication of durations of the at least two phases in the initial form.

57. The product of claim 53, wherein the instructions cause the computer to measure a lapse between a start indication and an end indication of at least one of the phases in the indication of the initial form.

58. The product of claim 57, wherein the start and end indications include respective audible indications of respiration of the subject, and wherein the instructions cause the computer to detect, via the user interface, the audible start and end indications.

59. The product of claim 57, wherein the instructions cause the computer to receive, via the user interface, the start and end indications from the subject at respective times, and to measure the lapse responsive thereto.

60. The product of claim 23, wherein the product is configured to have stored therein a plurality of exercise routines having respective initial forms and respective desired forms, and wherein the product further comprises an audio-playback device, configured to enable the subject to select one of the exercise routines.

61. The exercise device of claim 1, wherein the total duration of the exercise is set by the subject.

62. The exercise device of claim 1, wherein the duration of phase k of each transitional form of the plurality of transitional forms is determined by the following formula:

$$T_j[k] = T_{start}[k] + j * \Delta T[k]$$

where $$\Delta T[k] = (T_{end}[k] - T_{start}[k])/n$$

where j is the total duration of each biorhythmic activity pattern, $t_{start}$ is the total duration of the initial multiphase biorhythmic activity pattern, $T_{end}$ is the total duration of the a-priori determined desired multi-phase biorhythmic activity pattern, n is the number of the plurality of transitional forms.

63. The exercise device of claim 1, wherein the rate of phase k of each transitional form of the plurality of transitional forms is determined by the following formula:

$$1/T_j[k]=(1-e[k])*(1/T_{j-1}[k])$$

where j is the total duration of each biorhythmic activity pattern, e[k] is the selected change per biorhythmic pattern of phase ka and $1/T_j$ is the rate of biorhythmic pattern j.

* * * * *